(12) United States Patent
Muehlthau et al.

(10) Patent No.: US 9,447,036 B2
(45) Date of Patent: Sep. 20, 2016

(54) PROCESS FOR THE PREPARATION OF OPTIONALLY SUBSTITUTED PHENYL AND PYRIDYL PYRROLIDINES

(71) Applicant: BAYER CROPSCIENCE AG, Monheim (DE)

(72) Inventors: Friedrich August Muehlthau, Kelkheim-Fischbach (DE); Mark James Ford, Schmitten (DE)

(73) Assignee: Bayer Cropscience AG, Monheim (DE)

( * ) Notice: Subject to any disclaimer, the term of this patent is extended or adjusted under 35 U.S.C. 154(b) by 0 days.

(21) Appl. No.: 14/430,607

(22) PCT Filed: Sep. 25, 2013

(86) PCT No.: PCT/EP2013/069919
§ 371 (c)(1),
(2) Date: Mar. 24, 2015

(87) PCT Pub. No.: WO2014/048958
PCT Pub. Date: Apr. 3, 2014

(65) Prior Publication Data
US 2015/0246880 A1    Sep. 3, 2015

(30) Foreign Application Priority Data

Sep. 27, 2012  (EP) .................................... 12186243

(51) Int. Cl.

| | | |
|---|---|---|
| *C07F 7/08* | (2006.01) | |
| *C07D 207/08* | (2006.01) | |
| *C07C 317/10* | (2006.01) | |
| *C07C 317/14* | (2006.01) | |
| *C07C 317/18* | (2006.01) | |
| *C07C 323/07* | (2006.01) | |
| *C07C 323/16* | (2006.01) | |

(52) U.S. Cl.
CPC ........... *C07D 207/08* (2013.01); *C07C 317/10* (2013.01); *C07C 317/14* (2013.01); *C07C 317/18* (2013.01); *C07C 323/07* (2013.01); *C07C 323/16* (2013.01); *C07F 7/0812* (2013.01); *C07F 7/0818* (2013.01)

(58) Field of Classification Search
CPC . C07C 317/10; C07C 317/14; C07C 317/18; C07C 323/07; C07C 323/16; C07D 207/08; C07F 7/0818

See application file for complete search history.

(56) References Cited

U.S. PATENT DOCUMENTS

| | | | |
|---|---|---|---|
| 8,188,122 B2 | 5/2012 | Mihara et al. | |
| 8,450,483 B2 | 5/2013 | Goergens et al. | |
| 8,536,201 B2 | 9/2013 | Mihara et al. | |
| 8,785,647 B2 | 7/2014 | Goergens et al. | |
| 8,980,937 B2 | 3/2015 | Mihara et al. | |
| 2012/0129854 A1 | 5/2012 | Mihara et al. | |
| 2013/0310408 A1 | 11/2013 | Goergens et al. | |
| 2015/0011553 A1 | 1/2015 | Goergens et al. | |

FOREIGN PATENT DOCUMENTS

| | | | |
|---|---|---|---|
| WO | 2008128711 A1 | 10/2008 | |
| WO | 2010043315 A1 | 4/2010 | |
| WO | 2010124845 A1 | 11/2010 | |
| WO | 2011080211 A1 | 7/2011 | |
| WO | WO 2014/039489 | * | 3/2014 |

OTHER PUBLICATIONS

Smith, M. B. Organic Synthesis, McGraw-Hill, Inc. 1994, Chapter 1.*
International Search Report from corresponding PCT/EP2013/069919, mailed Nov. 14, 2013.
European Search Report from corresponding EP 12 18 6243, mailed Nov. 23, 2012.
Fakih et al., "Wittig-Horner Synthesis of Vinyl Sulfoxides from Aryl Alkyl or Diaryl Ketones under Sonication", J. prakt. Chem. 339 (1997), pp. 176-178, XP009165022.
Peters et al., "Competition between Isomerization and Addition in the Sonication of Vinyl Sulfones in the Presence of Bromotrichloromethane", J. prakt. Chem. 337 (1995) pp. 363-367, XP009165023.
Shen et al., "Stereospecific Synthesis of Trifluoromethylated Vinyl Sulfides", Synthesis 2005, No. 13, pp. 2183-2187, XP055045408.
Dellus et al., "An Isolable Mixed P,S-Bis(ylide) as an Asymmetric Carbon Atom Source", Angew. Chem. Int. Ed. 2010, 49, pp. 6798-6801, XP055045496.

* cited by examiner

*Primary Examiner* — Erich A Leeser
(74) *Attorney, Agent, or Firm* — McBee Moore Woodward Vanik, IP LLC

(57) ABSTRACT

The present invention relates to a method for the preparation of optionally substituted aryl and pyridyl pyrrolidines which are useful intermediates for the preparation of certain biologically active compounds.

11 Claims, No Drawings

PROCESS FOR THE PREPARATION OF OPTIONALLY SUBSTITUTED PHENYL AND PYRIDYL PYRROLIDINES

CROSS REFERENCE TO RELATED APPLICATIONS

This application is a §371 National Stage Application of PCT/EP2013/069919, filed Sep. 25, 2013, which claims priority to EP 12186243.7, filed Sep. 27, 2012.

BACKGROUND

1. Field of the Invention

The present invention relates to a method for the preparation of optionally substituted aryl and pyridyl pyrrolidines which are useful intermediates for the preparation of certain biologically active compounds.

2. Description of Related Art

It is known that certain aryl and heteroaryl pyrrolidines are useful for combating harmful pests such as insects, acari, helminthes and nematodes which occur in agriculture and in non-agriculture fields such as horticulture or in the field of veterinary medicine (cf. WO 2008/128711, WO 2010/124845, WO 2010/043315, WO 2011/080211).

SUMMARY

The present invention relates to a process for the preparation of compounds of formula (X)

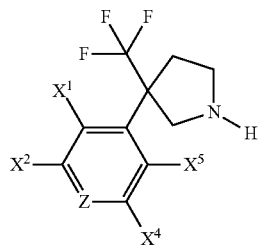

(X)

wherein Z, $X^1$, $X^2$, $X^4$ and $X^5$ and Q are as defined herein.

The method according to the invention comprises the following steps:

step (i): reacting trifluoroacetophenones of formula (II)

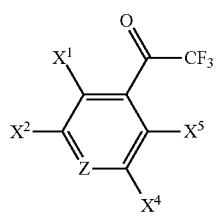

(II)

with compounds of formula (III)

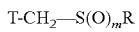

$T-CH_2-S(O)_mR$ (III)

optionally in the presence of a solvent, in the presence of a base (e.g. potassium tert-butoxide) and optionally in the presence of an additive, to obtain compounds of formula (IV), which includes both isomers of formula E-(IV) and Z-(IV)

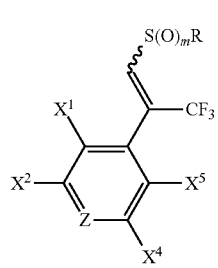

(IV)

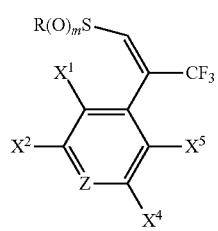

E-(IV)

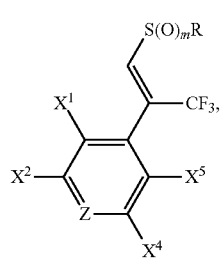

Z-(IV)

Step (ii): reacting compounds of the formula (IV), E-(IV), or Z-(IV)

(ii-a) with compounds of formula (V)

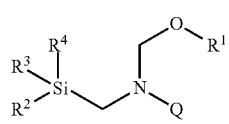

(V)

in the presence of an acid (e.g. $CF_3-CO_2H$) or a fluoride salt; or (ii-b) with compounds of formula (Va)

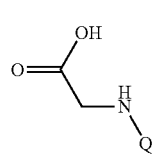

(Va)

in the presence of formaldehyde or a formaldehyde equivalent, (e.g. trioxane, paraformaldehyde), and in the presence of a solvent, in which process the water formed during the reaction is removed from the reaction mixture, (e.g. by continuously removing an azeotropic mixture (such as toluene and water) by distillation (in particular using a Dean-Stark apparatus)), to obtain compounds of formula (VI)

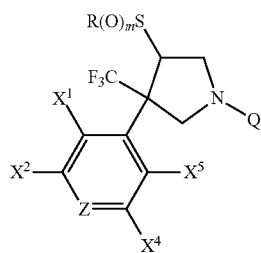

(VI)

which are converted into compounds of formula (I)

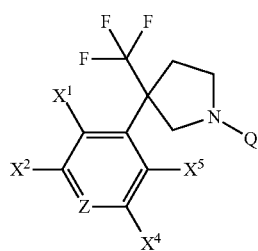

(I)

by (step (iii-a))

heating compounds of formula (VI) in which m represents 1, optionally in the presence of a base (e.g. triethylamine or sodium carbonate), if appropriate in the presence of a solvent (e.g. toluene) (step (iii-a-1)), to obtain compounds of formula (VII)

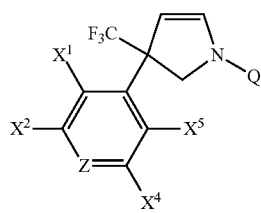

(VII)

which are subjected to a catalytic hydrogenation (e.g. using gaseous hydrogen in the presence of platinum on charcoal in methanol and in the presence of formic acid), or to a reduction reaction using a hydride source (e.g. sodium borohydride) in an appropriate solvent (e.g. tetrahydrofuran) (step (iii-a-2)) or, by (step (iii-b))

removing the $S(O)_mR$ group by reacting compounds of formula (VI) in which m represents 2, with an elemental metal in the presence of a solvent, and preferably in the presence of metal salts; or, by (step (iii-c))

removing the $S(O)_mR$ group from compounds of formula (VI) in which m represents 0 or 1 by catalytic hydrogenation in the presence of a solvent and optionally a base (e.g. triethylamine or sodium carbonate) or an acid (e.g. hydrochloric acid, acetic acid), and step (iv)

replacement of group Q by hydrogen to obtain compounds of formula (X), or compounds of formula (IV), which includes both isomers of formula E-(IV) and Z-(IV)

are reacted (step (ii-aa)) with compounds of formula (V-1)

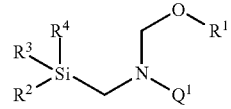

(V-1)

in the presence of an acid (e.g. $CF_3$—$CO_2H$) or a fluoride salt to obtain compounds of formula (VIa)

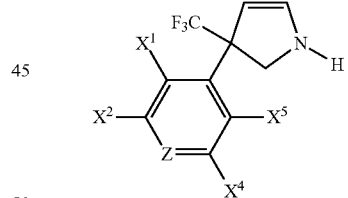

(VIa)

which are converted into compounds of formula (X)

by (step (iii-aa))

heating compounds of formula (VIa) in which m represents 1, optionally in the presence of a base (e.g. triethylamine or sodium carbonate), if appropriate in the presence of a solvent (e.g. toluene) (step (iii-aa-1)), to obtain compounds of formula (VIIa)

(VIIa)

which are subjected to a catalytic hydrogenation (e.g. using gaseous hydrogen in the presence of platinum on charcoal in methanol and in the presence of formic acid), or to a reduction reaction using a hydride source (e.g. sodium borohydride) in an appropriate solvent (e.g. tetrahydrofuran) (step (iii-aa-2)).

In formulae (I), (II), (III), (IV), (E-IV), (Z-IV), (V), (V-1), (Va), (VI), (VIa) (VII), (VIIa), and (X) the substituents or chemical groupings are defined as follows:

Z represents C—$X^3$ or a nitrogen atom; preferably Z is C—$X^3$;

$X^1$, $X^2$, $X^3$, $X^4$ and $X^5$ independently of each other are hydrogen, halogen (fluorine, chlorine, bromine, iodine), cyano, $C_1$-$C_{12}$-alkyl, $C_1$-$C_{12}$-haloalkyl, $C_1$-$C_{12}$-alkoxy or $C_1$-$C_{12}$-haloalkoxy; preferably $X^1$, $X^2$, $X^3$, $X^4$ and $X^5$, independently of each other, are hydrogen, fluorine, chlorine, bromine, iodine, $C_1$-$C_6$-alkyl, $C_1$-$C_6$-haloalkyl, $C_1$-$C_6$-alkoxy or $C_1$-$C_6$-haloalkoxy; more preferably $X^1$, $X^2$, $X^3$, $X^4$ and $X^5$ independently of each other are hydrogen, fluorine, chlorine, bromine, $C_1$-$C_4$-alkyl (methyl, ethyl, i-propyl, n-propyl, n-butyl, i-butyl, t-butyl), $C_1$-$C_4$-haloalkyl (in particular $CF_2H$, $CF_3$, $CH_2CF_3$, $CH_2CHF_2$), $C_1$-$C_4$-alkoxy (methoxy, ethoxy, i-propoxy) or $C_1$-$C_4$-haloalkoxy (in particular $OCF_2H$, $OCF_3$); most preferably $X^1$, $X^2$, $X^3$, $X^4$ and $X^5$, independently of each other are hydrogen, fluorine, chlorine, trifluoromethyl or methoxy;

$R^1$ is selected from the group consisting of $C_{1-12}$-alkyl, $C_{1-6}$-haloalkyl, phenyl, or phenyl-$C_{1-6}$-alkyl; preferably R is methyl, ethyl, phenyl, and benzyl;

$R^2$, $R^3$ and $R^4$ independently of each other are selected from the group consisting of $C_{1-12}$-alkyl, $C_{1-6}$-haloalkyl, phenyl, or phenyl-$C_{1-6}$-alkyl; preferably R is methyl, ethyl, phenyl, and benzyl;

Q is selected from the group consisting of aryl-$C_1$-$C_6$-alkyl, $C_1$-$C_6$-alkoxy-($C_1$-$C_6$)-alkyl, $C_1$-$C_6$-alkyl-(O—$CH_2$)$_n$, and $C_2$-$C_6$-alkenyl; preferably Q is selected from the group consisting of benzyl, $C_1$-$C_6$-alkoxy-($C_1$-$C_6$)-alkyl and $C_2$-$C_6$-alkenyl; more preferably Q is selected from the group consisting of benzyl, methoxymethyl and allyl;

$Q^1$ is selected from the group consisting of $C_1$-$C_6$-alkyl-(O—$CH_2$)$_n$, or $R^1$ and $Q^1$ together with the atoms to which they are attached form a ring selected from

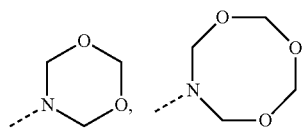

wherein the dotted line is the bond to the carbon atom adjacent to the Si-atom in formula (V-1);

T is an anion stabilizing group; preferably T is (($C_{1-4}$)-alkyl-(O)$_2$P(O), $A^-$ ($C_6H_5$)$_3P^+$, (($C_{1-4}$)-alkyl)$_3$Si; more preferably T is (EtO)$_2$P(O), $A^-$ ($C_6H_5$)$_3P^+$, or ($CH_3$)$_3$Si;

$A^-$ is chloride, bromide or iodide;

m is 0, 1 or 2;

n is 1 to 10; preferably n is 1 to 3; more preferably n is 1; and

R is $C_{1-12}$-alkyl, $C_{1-6}$-haloalkyl, phenyl, or phenyl-$C_{1-6}$-alkyl; preferably R is methyl, ethyl, phenyl, and benzyl.

DETAILED DESCRIPTION OF A PREFERRED EMBODIMENT

The compounds of formulae (I) or (X) can be used as intermediates to prepare biologically active compounds known from e.g. WO 2012/35011 A1, US 2012/129854 A1, WO 2011/80211 A1, WO 2010/43315 A1, and WO 2008/128711 A1.

The invention is further directed to an Embodiment [A] which comprises step (i), followed by step (i-a) as described below, and optionally by step (i-b) as described below, followed by steps (ii), and (iii-a) or (iii-b) and optionally step (iv).

Step (i-a): Compounds of formula (IVa)

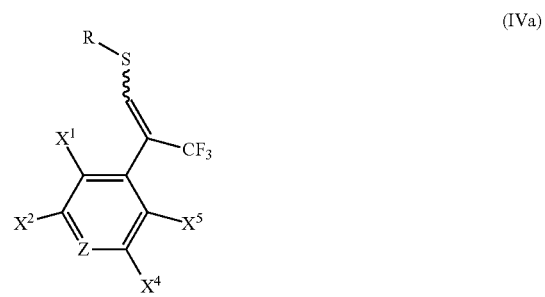

are reacted with an oxidizing agent (e.g. hydrogen peroxide in the presence of acetic acid or acetonitrile), optionally in the presence of a catalyst which may be a chiral catalyst to obtain compounds of formulae (IVb) and/or (IVc)

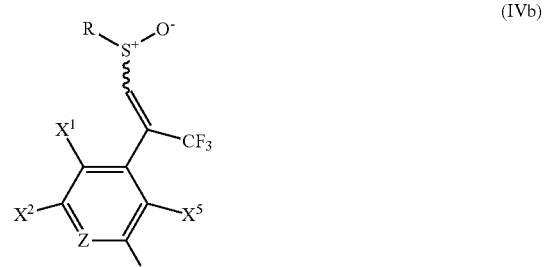

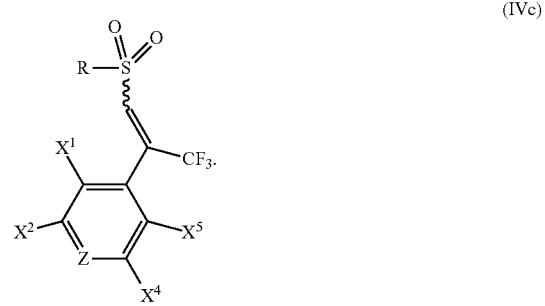

The invention is further directed to an Embodiment [B] which comprises step (i), followed by step (i-b) as described below, followed by steps (ii), and (iii-a) or (iii-b) and optionally step (iv).

Step (i-b): Compounds of formula (IVb)

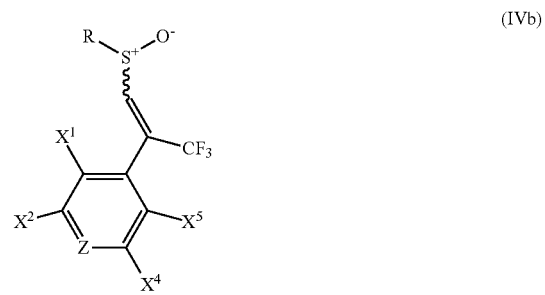

are reacted with the oxidizing agent of step (i-a), to obtain compounds of formula (IVc)

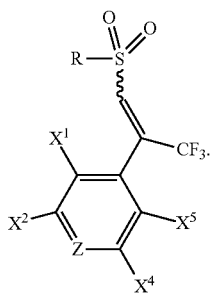

(IVc)

In another Embodiment [C] the compounds of formula (III) to be employed in step (i) are so-called "Wittig-salts" of formula (IIIa)

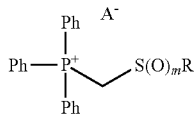

(IIIa)

wherein

Ph represents phenyl

R and m have the meanings as defined above, and

A represents chloride, bromide, or iodide.

This Embodiment [C] can certainly be combined with Embodiment [A] or [B].

In another Embodiment [D] the compounds of formula (III) to be employed in step (i) are phosphonates of formula (IIIb)

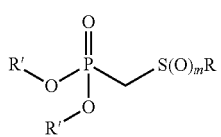

(IIIb)

wherein m, and R have the above mentioned meaning and both R' represent independently from each other alkyl, phenyl or benzyl.

Embodiment [D] can certainly be combined with Embodiment [A] or [B].

Another preferred Embodiment [E] is the combination of steps (iii-c) and (iv) in a one-pot-reaction. This can be achieved by a catalytic hydrogenation, in particular if Q is an optionally substituted benzyl group.

Another preferred Embodiment [F] is the combination of steps (iii-a-2) and (iv) in a one-pot-reaction. This can be achieved by a catalytic hydrogenation, in particular if Q is an optionally substituted benzyl group.

In another aspect of the invention, it is provided a stereo selective synthesis route for the compounds of formula (I) and (X).

To obtain selectively optical isomers, in particular the optical isomer of formula (I*)

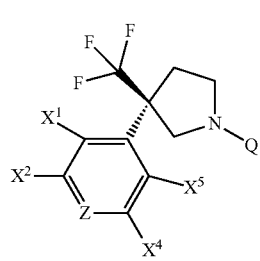

(I*)

wherein $X^1$, $X^2$, $X^4$, $X^5$, Z and Q have the above mentioned meanings and compounds of formula (E-IVb*):

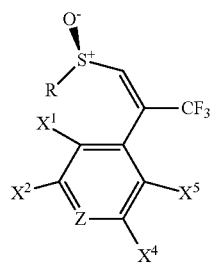

(E-IVb*)

in which $X^1$, $X^2$, $X^4$, $X^5$, R, and Z have the above mentioned meanings, are employed in step (ii) to obtain compounds of formula (VIb*)

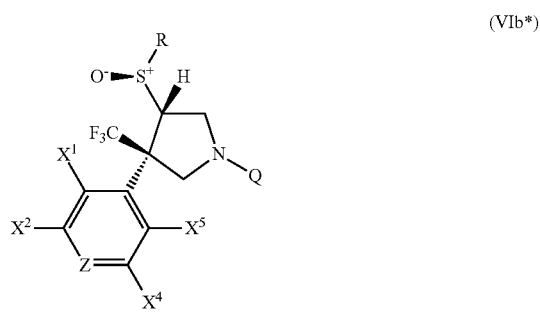

(VIb*)

wherein $X^1$, $X^2$, $X^4$, $X^5$, R, Q and Z have the above mentioned meanings.

It was surprisingly found that the stereo chemical information of the compound of formula (IVb*) is almost fully transferred to the resulting compound of formula (VIb*). The compounds of formula (VI) in their desired stereo chemical form can be obtained in an optical purity of at least 70%. The method according to the invention is thus particularly useful for the stereo selective synthesis of compounds having the stereochemistry depicted within the circle in the following formula:

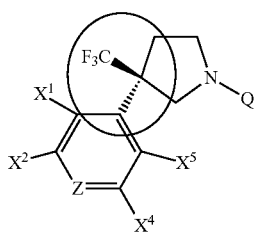

The stereo selective method according to the present invention is illustrated in reaction scheme 1:

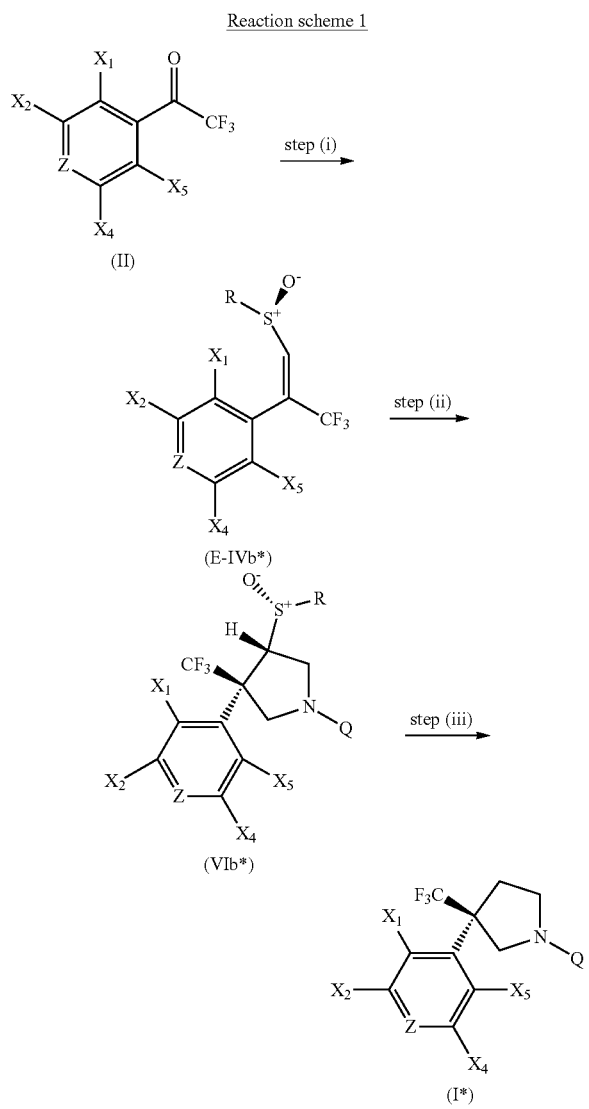

Reaction scheme 1

The compounds of formula (I*) can be converted to compounds of formula (X*) by applying the reaction conditions according to step (iv), thereby preserving the stereochemistry of the compounds of formula (I*).

Trifluoro acetophenones of formula (II) are commercially available or can be prepared by methods known in the art (cf. WO2010/86820 A1; U.S. Pat. No. 6,096,926 A1; WO2003/99805 A1).

Compounds of formula (III) are commercially available or can be prepared by methods known in the art (for compounds of formula (IIIa) cf. U.S. Pat. No. 4,173,463 B; Chemische Berichte 1983, 116, 1955-1962; for compounds of formula (IIIb) cf. WO 2010/99379 A1; US 2006/241057 A1; Synthesis 1990, 10, 937-938; U.S. Pat. No. 4,092,349).

The reactions according to steps (i), (ii), (iii) and (iv) can be conducted at reduced pressure (below 1 bar), under vacuum (below 0.4 bar), under increased pressure (above 1 bar) or under normal pressure (i.e. around 1 bar). It is preferred to conduct the reactions under normal pressure. Catalytic hydrogenations are preferably conducted under normal pressure or under increased pressure.

The reaction according to step (i) can be conducted in the absence or in the presence of a solvent. It is preferred to conduct the reaction according to step (i) in the presence of a solvent. Suitable solvents include aliphatic and aromatic hydrocarbons (e.g. n-hexane, benzene, toluene, xylene) which can be substituted by fluorine or chlorine (e.g. methylenchloride, dichloromethane, $CCl_4$, fluorobenzene, chlorobenzene or dichlorobenzene); ethers (e.g. diethylether, diphenylether, methyl-tert-butylether, isopropylethylether, dioxane, dimethylglycol, THF or methyltetrahydrofuran); nitriles (e.g. methyl nitrile (acetonitrile, butyl nitrile or phenyl nitrile); and alcohols (e.g. ethanol or isopropanol).

For the reaction of the Wittig-salts of formula (IIIa) (cf. also Embodiment [C]) the preferred solvents are benzene, toluene and xylene. For the reaction of the phosphonates of formula (IIIb) (cf. also Embodiment [D]) the preferred solvents are methyl nitrile, butylnitrile, tetrahydrofuran (THF) and methyltetrahydrofuran.

The reaction according to step (i) using the Wittig-salts of formula (IIIa) (cf. also Embodiment [C]) is conducted in the presence of a base and optionally in the presence of a phase transfer catalyst or a solubilising agent. Examples of bases which may be used in step (i) using the Wittig-salts of formula (IIIa) include alkali metal bases (e.g. lithium hydride, sodium hydride, potassium hydride, butyl lithium, tert-butyl lithium, trimethylsilyl lithium, lithium hexamethyldisilazide, sodium carbonate, potassium carbonate, cesium carbonate, tripotassium phosphate, sodium acetate, potassium acetate, sodium methoxide, sodium ethoxide, sodium-tert-butoxide and potassium-tert-butoxide), organic bases (e.g. triethylamine, diisopropylethylamine, tributylamine, N-methylmorpholine, N,N-dimethylaniline, N,N-diethylaniline, 4-tert-butyl-N,N-dimethylaniline, pyridine, picoline, lutidine, diazabicyclooctan (DABCO), diazabicyclononen (DBN), diazabicycloundecen (DBU) and imidazole). Preferred bases are sodium tert-butoxide, potassium tert-butoxide, sodium carbonate, and potassium carbonate.

Examples for phase transfer catalysts or solubilising agents which may be used in step (i) using the Wittig-salts of formula (IIIa) include quaternary ammonium salts (e.g. tetramethyl ammonium chloride, tetrabutyl ammonium chloride, tetrabutyl ammonium bromide), and polyethers (e.g. 18-crown-6, polyethylene glycol). Preferred phase transfer catalyst or solubilising agent is polyethylene glycol.

The reaction of step (i) using the posphonate of formula (IIIb) is conducted in the presence of a base and optionally in the presence of a Lewis acid. Examples of the bases which may be used in step (i) using the posphonate (IIIb) include alkali metal bases (e.g. lithium hydride, sodium hydride, potassium hydride, butyl lithium, tert-butyl lithium, trimethylsilyl lithium, lithium hexamethyldisilazide, sodium carbonate, potassium carbonate, cesium carbonate, tripotassium phosphate, sodium acetate, potassium acetate, sodium methoxide, sodium ethoxide, sodium-tert-butoxide and potassium-tert-butoxide), organic bases (e.g. triethylamine, diisopropylethylamine, tributylamine, N-methylmorpholine, N,N-dimethylaniline, N,N-diethylaniline, 4-tert-butyl-N,N-dimethylaniline, pyridine, picoline, lutidine, diazabicyclooctan (DABCO), diazabicyclononen (DBN), diazabicycloundecen (DBU) and imidazole). Preferred bases are sodium-tert-butoxide, and potassium-tert-butoxide for use without Lewis acid and triethylamine, diisopropylethylamine, and tributylamine for the use with Lewis acid. Examples of Lewis acids which may be used in step (i) using the posphonate of formula (IIIb) include alkali metal halides (e.g. lithium chloride, lithium bromide, potassium chloride), alkaline earth metal halides (e.g. magnesium chloride, magnesium bromide, calcium chloride). Preferred Lewis acids are lithium chloride, lithium bromide, and magnesium chloride.

Step (i-a) as well as step (i-b) can be conducted by applying the procedures disclosed in US 2011/0015405 A1. This document is incorporated herein by reference.

Suitable oxidizing agents are known in the art and are those which are capable of oxidizing sulphur compounds to the corresponding sulfoxide and/or sulfone compounds. Suitable oxidizing agents which can be used in step (i-a) as well as in step (i-b) are, for example, inorganic peroxides like hydrogen peroxide, or organic peroxides, for example $C_1$-$C_6$-alkyl hydroperoxides and aryl-($C_1$-$C_6$)-alkyl hydroperoxides. Further suitable oxidizing agents are sodium periodate or sodium perborate, The preferred oxidizing agent is hydrogen peroxide. The molar ratio of oxidizing agent to the compound of formula (IVa) or (IVb), if the latter is used in step (i-b) as starting material, is in the range from 0.9:1 to 4:1, preferably between 1.0:1 and 2.5:1.

Suitable chiral catalysts are chiral metal-ligand complexes, where the metal is a transition metal derivative and the ligand is a chiral compound of formula (C-1) or (C-2) (in below formulae, chiral carbon atoms are marked with an asterisk (*)),

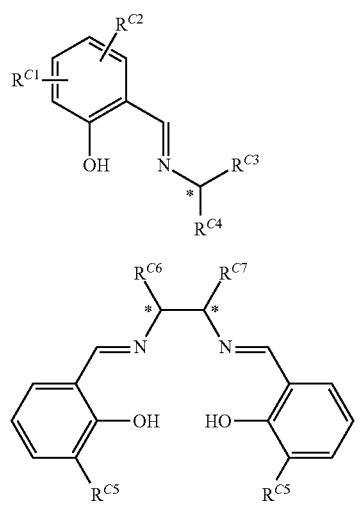

in which
$R^{C1}$ and $R^{C2}$ are independently from each other selected from the group consisting of hydrogen, ($C_1$-$C_6$)-alkyl, ($C_1$-$C_6$)-alkylphenyl, phenyl, halogen, cyano, nitro, cyano-($C_1$-$C_6$)-alkyl, hydroxy-($C_1$-$C_6$)-alkyl, ($C_1$-$C_6$)-alkoxycarbonyl-($C_1$-$C_6$)-alkyl, ($C_1$-$C_6$)-alkoxy-($C_1$-$C_6$)-alkyl, $R^{C3}$ is selected from the group consisting of ($C_1$-$C_6$)-alkyl, halogen-, cyano-, nitro-, amino-, hydroxyl- or phenyl-substituted ($C_1$-$C_6$)-alkyl, carboxyl, carbonyl-($C_1$-$C_6$)-alkyl, ($C_1$-$C_6$)-alkoxycarbonyl-($C_1$-$C_6$)-alkyl, ($C_1$-$C_6$)-alkoxy-($C_1$-$C_6$)-alkyl, ($C_1$-$C_6$)-alkoxy, di-($C_1$-$C_6$)-alkoxy-($C_1$-$C_6$)-alkyl, $R^{C4}$ is selected from the group consisting of hydrogen, ($C_1$-$C_6$)-alkyl, ($C_1$-$C_6$)-alkylphenyl, phenyl, phenyl-($C_1$-$C_6$)-alkyl, preferably from the group consisting of tert-butyl, iso-propyl, benzyl, phenyl;

$R^{C5}$ is selected from the group consisting of hydrogen, ($C_1$-$C_6$)-alkyl, ($C_1$-$C_6$)-alkylphenyl, phenyl, halogen, cyano, nitro, cyano-($C_1$-$C_6$)-alkyl, hydroxy-($C_1$-$C_6$)-alkyl, ($C_1$-$C_6$)-alkoxycarbonyl-($C_1$-$C_6$)-alkyl, ($C_1$-$C_6$)-alkoxy-($C_1$-$C_6$)-alkyl, $R^{C6}$ and $R^{C7}$ are independently from each other selected from the group consisting of hydrogen, ($C_1$-$C_6$)-alkyl, phenyl, or $R^{C6}$ and $R^{C7}$ may form a bridge, e.g. consisting of butane-1,4-diyl or a methylene ($C_1$-$C_6$)-alkyl amino methylene unit.

In general, the chiral ligand is a chiral compound which is capable, for example, of reacting with transition metal derivatives. Such compounds are preferably selected from chiral alcohols. Preferred chiral ligands include the Schiff bases of formulae (C-1) and (C-2). These Schiff bases can form a chiral metal-ligand complex.

Transition metal derivatives are preferably vanadium derivatives, molybdenum derivatives, zirconium derivatives, iron derivatives, manganese derivatives and titanium derivatives, very preferably vanadium derivatives. These derivatives can be used, for example, in the form of the transition metal (IV) halides, transition metal (IV) alkoxides or transition metal(IV) acetylacetonates.

The chiral transition metal complex is obtained by reaction of a transition metal derivative and a chiral ligand, separately or in the presence of the compound of formula (IVa) or (IVb), if the latter is used as starting material.

The amount of the chiral metal-ligand complex is in the range from 0.001 to 10 mol %, preferably from 0.1 to 5 mol %, most preferably 1 to 4 mol %, in relation to the amount of the compound of formula (IVa), if the latter is used as starting material. A higher amount of chiral metal-ligand complex can be used but is usually economically unviable.

Step (i-a) as well as step (i-b) can be performed in the presence of a solvent. Suitable solvents include: THF, dioxane, diethyl ether, diglyme, methyl tert-butyl ether (MTBE), tert-amyl methyl ether (TAME), dimethyl ether (DME), 2-methyl-THF, acetonitrile, butyronitrile, toluene, xylenes, mesitylene, ethyl acetate, isopropyl acetate, alcohols such as methanol, ethanol, propanol, butanol, ethylene glycol, ethylene carbonate, propylene carbonate, N,N-dimethylacetamide, N,N-dimethylformamide, N-methylpyrrolidone, halohydrocarbons and aromatic hydrocarbons, especially chlorohydrocarbons such as tetrachloroethylene, tetrachloroethane, dichloropropane, methylene chloride, dichlorobutane, chloroform, carbon tetrachloride, trichloroethane, trichloroethylene, pentachloroethane, difluorobenzene, 1,2-dichloroethane, chlorobenzene, bromobenzene, dichlorobenzene, chlorotoluene, trichlorobenzene; 4-methoxybenzene, fluorinated aliphatics and aromatics such as trichlorotrifluoroethane, benzotrifluoride, 4-chlorobenzotrifluoride, acetic acid and water. It is also possible to use mixtures of solvents.

Step (i-a) as well as step (i-b) are generally performed at a temperature between −80° C. and 200° C., preferably between 0° C. and 140° C., more preferably between 10° C.

and 60° C., and at a pressure up to 100 bar, more preferably at a pressure between standard pressure and 40 bar.

Step (i-a) as well as step (i-b) can for example be conducted under reaction conditions as provided in the following table, wherein VO(acac)$_2$ means vanadyl acetylacetonate, RT stands for room temperature (i.e around 20° C.), and Fe(acac)$_3$ means Iron(II)acetylacetonate. Preferred combinations of transition metal derivatives and chiral ligands (catalyst systems) are depicted in the following table.

| Catalyst system | | Oxidizing agent | Solvent | T |
|---|---|---|---|---|
| VO(acac)$_2$ / | [tBu-salicylaldimine ligand] | H$_2$O$_2$ | CH$_3$CN | RT |
| Fe(acac)$_3$ / | [diiodo-salicylaldimine ligand] | H$_2$O$_2$ | CH$_2$Cl$_2$ | RT |
| | [chiral Mn-salen complex] | H$_2$O$_2$ | CH$_3$CN | 40° C. |

In a preferred embodiment of step (ia), compounds of formula E-(IVa) are converted to compounds of formula E-(IVb) in the presence of vanadyl acetylacetonate (VO(acac)$_2$) and H$_2$O$_2$ together with 2,4-di-tert-butyl-6-[(E)-{[(2S)-1-hydroxy-3,3-dimethylbutan-2-yl]imino}methyl]phenol in an appropriate solvent, preferably acetonitril, as depicted in reaction scheme 2.

Reaction scheme 2:

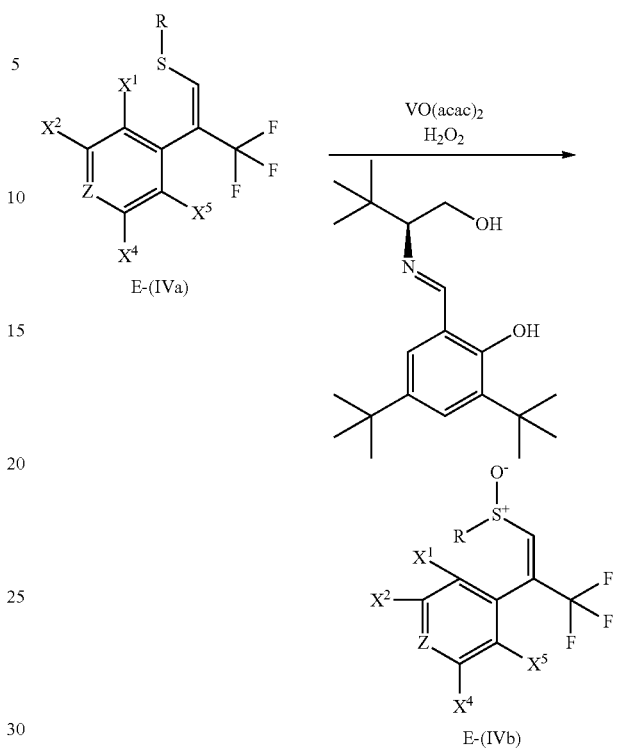

in which X$^1$, X$^2$, X$^4$, X$^5$, Z, and R have the above mentioned meanings.

Preferred solvents for the reaction according to step (i) in Embodiment [B] are methyl nitrile, butyl nitrile, tetrahydrofuran or methyl tetrahydrofuran or mixtures thereof.

Step (i-a) takes place in the presence of an oxidizing agent. Suitable oxidizing agents are for example inorganic peroxides like hydrogen peroxide, or organic peroxides, for example C$_1$-C$_6$ alkyl hydroperoxides and aryl-(C$_1$-C$_6$)-alkyl hydroperoxides. Hydrogen peroxide in water (35-50%) is preferred.

If hydrogen peroxide is used as oxidizing agent in step (i-a) without a chiral catalyst, then it is preferred to use glacial acetic acid as solvent.

Compounds of formula (V) are commercially available or can be prepared by methods known in the art (US2006/128789 A1, 2006; US2008/234280 A1, 2008; US2008/9619 A1, 2008; WO2009/87058 A1, 2009). Compounds of formula (Va) are commercially available or can be prepared by methods known in the art (U.S. Pat. No. 5,827,881 A1, 1998; WO2006/130418 A1, 2006; U.S. Pat. No. 5,071,999 A1, 1991; WO2008/62182 A1, 2008; WO2009/111997 A1, 2009).

The reaction according to step (ii) can be conducted in the absence or in the presence of a solvent. It is preferred that the reaction according to step (ii) is conducted in the presence of a solvent. Suitable solvents include aliphatic and aromatic hydrocarbons (e.g. n-hexane, benzene, toluene, xylene) which can be substituted by fluorine or chlorine (e.g. methylenchloride, dichlormethane, CCl$_4$, fluorobenzene, chlorobenzene or dichlorobenzene); ethers (e.g. diethylether, diphenylether, methyl-tert-butylether, isopropylethylether, dioxane, dimethylglycol, THF or methyl tetrahydrofuran); nitriles (e.g. methyl nitrile, butyl nitrile or phenyl nitrile); and alcohols (e.g. ethanol or isopropanol). For the reaction of compounds of formula (V) the preferred solvents are benzene, toluene, methylenchloride, and methyl nitrile. For the reaction of compounds (Va) the preferred solvents are benzene, toluene and xylene.

The reaction according to step (ii-a) using the compounds of formula (V) is conducted in the presence of an acid or a fluoride salt. Examples of acids include carboxylic acids (e.g. acetic acid, formic acid), halogenated carboxylic acids (e.g. trichloro acetic acid, trifluoroacetic acid), sulfonic acids (e.g. methylsulfonic acid, phenylsulfonic acid, p-toluenesulfonic acid, and camphorsulfonic acid). Trifluoroacetic acid is the preferred acid.

Examples of fluoride salts which may be used in step (ii-a) using the compounds of formula (V) include alkali metal fluorides (e.g. lithium fluoride, sodium fluoride, caesium fluoride), alkylammonium fluorides (e.g. tetramethyl ammonium fluoride, tetraethyl ammonium fluoride, and tetrabutyl ammonium fluoride). Preferred are tetrabutyl ammonium fluoride and sodium fluoride.

The reaction according to step (ii-b) using the compounds of formula (Va) is conducted in the presence of formaldehyde or a formaldehyde equivalent. Examples for formaldehyde equivalents which may be used in step (ii-b) using the compounds of formula (Va) include oligomeric or polymeric formaldehyde (e.g. 1,3,5-trioxane, para-formaldehyde). In all cases the water generated during the reaction is removed. An example for a method to remove the water from the reaction is the azeotropic distillation of toluene and water continuously using a Dean-Stark apparatus.

Suitable catalysts to be used for the catalytic hydrogenation in step (iii-a-2), step (iii-c) and in step (iv) comprise one or more metals of groups 8-10 of the Periodic Table, especially one or more metals selected from iron, ruthenium, osmium, cobalt, rhodium, iridium, nickel, palladium and platinum. Besides their catalytic activity, suitable catalysts are under the selected reaction conditions inert. The metals may be present in any chemical form, for example in elemental, colloidal, salt or oxide form, together with complexing agents as chelates, or as alloys, in which case the alloys may also include other metals, for example aluminium, as well as the metals listed above. The metals may be present in supported form, i.e. applied to any support, preferably an inorganic support. Examples of suitable supports are carbon (charcoal or activated carbon), aluminium oxide, silicon dioxide, zirconium dioxide or titanium dioxide. Catalysts preferred in accordance with the invention contain one or more metals of groups 8-10 of the Periodic Table on an inorganic support. Particular preference is given in accordance with the invention to catalysts which include palladium and platinum, and are optionally applied to an inorganic support (e.g. carbon). Such catalysts are, for example platinum on carbon, platinum oxide on carbon and palladium on carbon.

In the catalytic hydrogenation according to step (iii-c), step (iii-a-2) and step (iv) the catalyst is used in an amount of about 0.01 to about 30% by weight based on compounds of formula (VI) respectively compounds of formula (VII). The catalyst is preferably used in a concentration of about 0.1 to about 15% by weight.

The catalytic hydrogenation can be performed under elevated pressure (i.e. up to about 200 bar) in an autoclave, or at standard pressure in a hydrogen gas atmosphere. Especially at high reaction temperatures, it may be helpful to work at elevated pressure. The (additional) pressure increase can be brought about by supply of an inert gas, such as nitrogen or argon. The inventive hydrogenation is effected preferably at a pressure in the range from about 1 to about 30 bar, more preferably at a pressure in the range from about 5 to about 25 bar.

It is generally advantageous to perform the catalytic hydrogenation in the presence of solvents (diluents). However, the catalytic hydrogenation can also be performed without a solvent. Solvents are advantageously used in such an amount that the reaction mixture can efficiently be stirred over the entire process. Advantageously, based on compound (VI) or (VII) used, 1 to 50 times the amount of solvent, preferably 2 to 40 times the amount of solvent and more preferably 2 to 30 times the amount of solvent is used.

Useful solvents for performance of catalytic hydrogenation of step (iii-a-2), step (iii-c) and step (iv) according to the invention include all organic solvents which are inert under the reaction conditions, the type of solvent used depending on the type of reaction procedure, more particularly on the type of catalyst used and/or the hydrogen source (introduction of gaseous hydrogen or generation in situ). Mixtures of solvents can also be used.

Solvents suitable for the catalytic hydrogenation of step (iii-a-2), step (iii-c) and step (iv) are halohydrocarbons, e.g. chlorohydrocarbons, such as tetrachloroethylene, tetrachloroethane, dichloropropane, methylene chloride, dichlorobutane, chloroform, carbon tetrachloride, trichloroethane, trichloroethylene, pentachloroethane, difluorobenzene, 1,2-dichloroethane, chlorobenzene, bromobenzene, dichlorobenzene, chlorotoluene, trichlorobenzene; alcohols such as methanol, ethanol, isopropanol, butanol; ethers, such as ethyl propyl ether, methyl tert-butyl ether, n-butyl ether, anisole, phenetole, cyclohexyl methyl ether, dimethyl ether, diethyl ether, dimethylglycol, diphenyl ether, dipropyl ether, diisopropyl ether, di-n-butyl ether, diisobutyl ether, diisoamyl ether, ethylene glycol dimethyl ether, isopropyl ethyl ether, methyl tert-butyl ether, tetrahydrofuran, dioxane, dichlorodiethyl ether, and polyethers of ethylene oxide and/or propylene oxide; aliphatic, cycloaliphatic or aromatic hydrocarbons such as pentane, hexane, heptane, octane, nonane, and technical-grade hydrocarbons which may be substituted by fluorine and chlorine atoms, such as methylene chloride, dichloromethane, trichloromethane, carbon tetrachloride, fluorobenzene, chlorobenzene or dichlorobenzene; for example white spirits having components with boiling points in the range, for example, from 40° C. to 250° C., cymene, petroleum fractions within a boiling range from 70° C. to 190° C., cyclohexane, methylcyclohexane, petroleum ether, ligroin, octane, benzene, toluene, chlorobenzene, bromobenzene, xylene; esters such as methyl acetate, ethyl acetate, butyl acetate, isobutyl acetate, and also dimethyl carbonate, dibutyl carbonate or ethylene carbonate. Another solvent is water.

The catalytic hydrogenation according to step (iii-a-2), step (iii-c) and step (iv) can optionally be performed in the presence of acids or bases. Acids suitable for the catalytic hydrogenation are inorganic acids, such as hydrochloric acid, hydrobromic acid, sulphuric acid, phosphoric acid; organic acids, such as acitic acid, trichloro acetic acid, trifluoro acetic acid and benzoic acid. Bases suitable for the catalytic hydrogenation are inorganic bases, e.g. alkali metal carbonates, such as sodium carbonate, potassium carbonate; alkaline earth metal carbonates, such as calcium carbonate; organic bases, e.g. alkylamines, such as triethylamine and ethyl di-iso-propyl amine.

In the catalytic hydrogenation according to step (iii-a-2), step (iii-c) and step (iv) according to the invention, the solvents used are preferably ethers or alcohols.

The catalytic hydrogenation according to step (iii-a-2), step (iii-c) and step (iv) can be performed within a wide temperature range (for example in the range from about −20° C. to about 100° C.). Preference is given to performing the catalytic hydrogenation within a temperature range from about 0° C. to about 100° C., in particular room temperature (i.e. around 20° C.).

The reaction according to step (iii-b) is conducted in the presence of a metal. Examples for metals include alkali metals (e.g. sodium), alkaline earth metals (e.g. magnesium), and transition metals (e.g. zink). Preferred metal is magnesium.

In the catalytic hydrogenation according to step (iii-a-2), step (iii-c) and step (iv) according to the invention, the solvents used are preferably ethers or alcohols.

The catalytic hydrogenation according to step (iii-a-2), step (iii-c) and step (iv) can be performed within a wide temperature range (for example in the range from about −20° C. to about 100° C.). Preference is given to performing the catalytic hydrogenation within a temperature range from about 0° C. to about 100° C., in particular room temperature (i.e. around 20° C.).

The reaction according to step (iii-b) is conducted in the presence of a metal. Examples for metals include alkali metals (e.g. sodium), alkaline earth metals (e.g. magnesium), and transition metals (e.g. zink). Preferred metal is magnesium.

The reaction according to step (iii-b) is optionally conducted in the presence of a metal salt. Examples for metals include alkali metal halides (e.g. lithium chloride), alkaline earth metal halides (e.g. magnesium chloride), and transition metal salts (e.g. zink chloride). Preferred metal salt is lithium chloride.

The reaction according to step (iii-b) can be conducted in the absence or in the presence of a solvent. It is preferred to conduct the reaction according to step (iii-b) in the presence of a solvent. Suitable solvents include aliphatic and aromatic hydrocarbons (e.g. n-hexane, benzene, toluene, xylene); ethers (e.g. diethylether, diphenylether, methyl-tert-butylether, isopropylethylether, dioxane, dimethylglycol, THF or methyltetrahydrofuran); nitriles (e.g. methyl nitrile, butyl nitrile or phenyl nitrile), organic acids (e.g. acetic acid) and alcohols (e.g. ethanol or isopropanol). Preferred solvents are methanol, ethanol, isopropanol, THF, and acetic acid.

The reaction according to step (iii-a-1) is conducted in the presence of a base. Suitable bases include alkali metal salts (e.g. sodium carbonate, potassium carbonate, cesium carbonate, tripotassium phosphate, sodium acetate, potassium acetate, sodium methoxide, sodium ethoxide, sodium-tert-butoxide and potassium-tert-butoxide), organic bases (e.g. triethylamine, diisopropylethylamine, tributylamine, N-methylmorpholine, N,N-dimethylaniline, N,N-diethylaniline, 4-tert-butyl-N,N-dimethylaniline, pyridine, picoline, lutidine, diazabicyclooctan (DABCO), diazabicyclononen (DBN), diazabicycloundecen (DBU) and imidazole). Preferred bases are sodium carbonate, potassium carbonate, and triethylamine.

The reaction according to step (iii-a-1) can be conducted in the absence or in the presence of a solvent. It is preferred that the reaction according to step (iii-a-1) is conducted in the presence of a solvent. Suitable solvents include aliphatic and aromatic hydrocarbons (e.g. n-hexane, benzene, toluene, xylene); ether (e.g. diethylether, diphenylether, methyl-tert-butylether, isopropylethylether, dioxane, dimethylglycol, THF or methyltetrahydrofuran); nitriles (e.g. methyl nitrile, butylnitrile or phenylnitrile); organic acids (e.g. acetic acid) and alcohols (e.g. ethanol or isopropanol). Preferred solvents are benzene, toluene, and xylene.

In the reaction according to step (iii-a-2) the double bond of the compound of formula (VII) is reduced by catalytic hydrogenation in an appropriate solvent.

Alternatively the compound of formula (VII) can be reacted in step (iii-a-2) with a hydride source to reduce the double bond. Examples for hydride sources include hydrides (e.g. borane), hydride complexes (e.g. borane dimethylsulfide complex, borane tetrahydrofurane complex), mixed hydrides (e.g. lithium aluminium hydride, sodium borohydride, sodium cyano borohydride, sodium tri-acetoxy borohydride), and alkylaluminium hydrides (e.g. diisobuthylaluminiumhydride [DIBAL]). Preferred hydride sources are sodium borohydride and borane complexes.

The reaction according to step (iii-a-2) can be conducted in the absence or in the presence of a solvent. It is preferred that the reaction according to step (iii-a-2) is conducted in the presence of a solvent. Suitable solvents include for example aliphatic and aromatic hydrocarbons (e.g. n-hexane, benzene, toluene, xylene); ether (e.g. diethylether, diphenylether, methyl-tert-butylether, isopropylethylether, dioxane, dimethylglycol, THF or methyltetrahydrofuran); nitriles (e.g. methyl nitrile, butylnitrile or phenylnitrile), organic acids (e.g. acetic acid) and alcohols (e.g. ethanol or isopropanol). Preferred solvents are THF, methyltetrahydrofurane and methyl nitrile.

Methods for the cleavage of Q (step (iv)) are described in the literature (e.g. Philip J. Kocienski, *Protecting Groups*, Thieme, Stuttgart, 2005; Peter G. M. Wuts and Theodora W. Greene, Greene's *Protective Groups in Organic Synthesis*, John Wiley & Sons, 2006). Substituted methylen phenyl (benzyl) groups can be removed by catalytic hydrogenation (see above) or by treating the compound with 1-chloroethyl carbonochloridoate and subsequently with methanol (procedure see WO2008/128711 A1, WO2012/35011 A1).

The invention is illustrated by the following examples without limiting the invention to the same.

The following abbreviations are used: MW=molecular weight, MS=mass spectrometry, GC=gas chromatography, NMR=nuclear magnetic resonance.

The analytical data given below have been collected using the following instruments:

NMR: Bruker Avance III (400 MHz) or BRUKER Avance III (600 MHz), measured at 300K;

MS: Waters Acquity UPLC with 3100 Mass Detector.

GC: Perkin Elmer Autosystem XL, column: HP5, carrier gas: helium

PREPARATION EXAMPLE 1

Embodiment [C]

Step (i)—Preparation of 2-(3,5-dichlorophenyl)-3,3, 3-trifluoroprop-1-en-1-yl phenyl sulfide

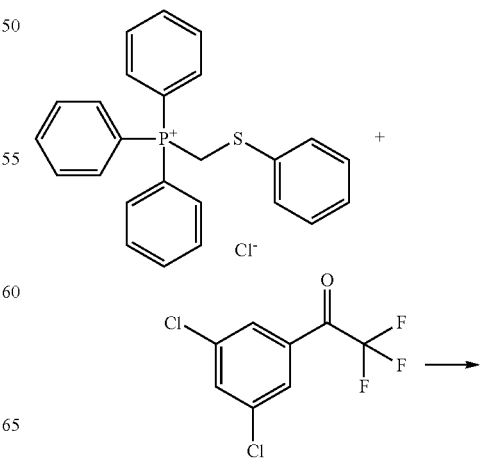

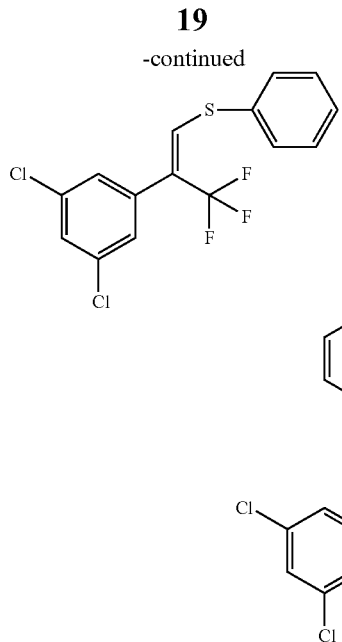

Triphenyl[(phenylsulfanyl)methyl]phosphonium chloride (50.0 g, 116 mmol) and potassium carbonate (32.2 g, purity 98%, 233 mmol) were suspended in toluene (1 L) under an inert gas atmosphere (argon) and cooled to 5° C. 1-(3,5-Dichlorophenyl)-2,2,2-trifluoroethanone (29.5 g, purity 96%, 116 mmol) and polyethyleneglycole (MW 1500, 8.76 g, 5.82 mmol) were added and the reaction mixture was stirred for five and a half hours at 5° C. and after warming to room temperature stirred for additional two hours. Water (500 mL) was added and the phases were separated. The water phase was extracted with toluene and the combined organic phases were washed with water (2x) and brine. After drying over sodium sulfate, filtration and evaporation the crude mixture was treated with n-heptane (250 mL) and left in the freezer overnight. The solid was filtered off and the solvents of the filtrate were evaporated. This material was again taken up in n-heptane (100 mL) and kept in the freezer for three days. Filtration and evaporation of the solvent gave 2-(3,5-dichlorophenyl)-3,3,3-trifluoroprop-1-en-1-yl phenyl sulfide (41.6 g, 96% purity, 99% yield; E/Z=94/6—determined by GC).

$^1$H-NMR (CDCl$_3$, 400 MHz): δ=6.98 (s, 1H), 7.30-7.47 ppm (m, 8H); MS (EI+): m/z=347.9 [M$^+$].

PREPARATION EXAMPLE 1A

Step (i)—Preparation of [(3,3,3-trifluoro-2-phenyl-prop-1-en-1-yl)sulfanyl]benzene

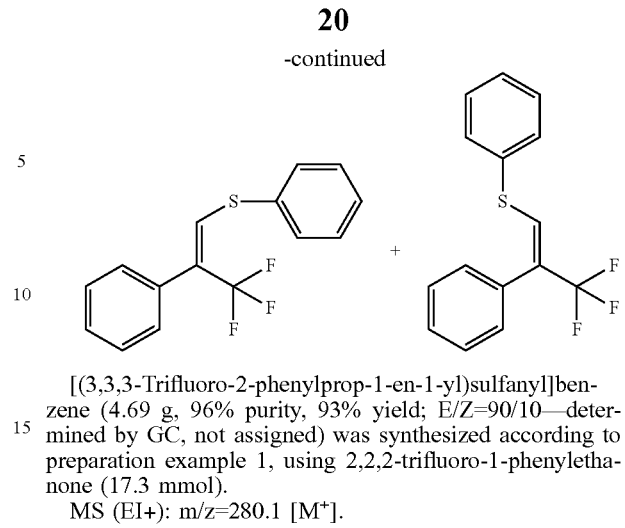

[(3,3,3-Trifluoro-2-phenylprop-1-en-1-yl)sulfanyl]benzene (4.69 g, 96% purity, 93% yield; E/Z=90/10—determined by GC, not assigned) was synthesized according to preparation example 1, using 2,2,2-trifluoro-1-phenylethanone (17.3 mmol).

MS (EI+): m/z=280.1 [M$^+$].

PREPARATION EXAMPLE 1B

Step (i)—Preparation of 1-methoxy-4-[3,3,3-trifluoro-1-(phenylsulfanyl)prop-1-en-2-yl]benzene

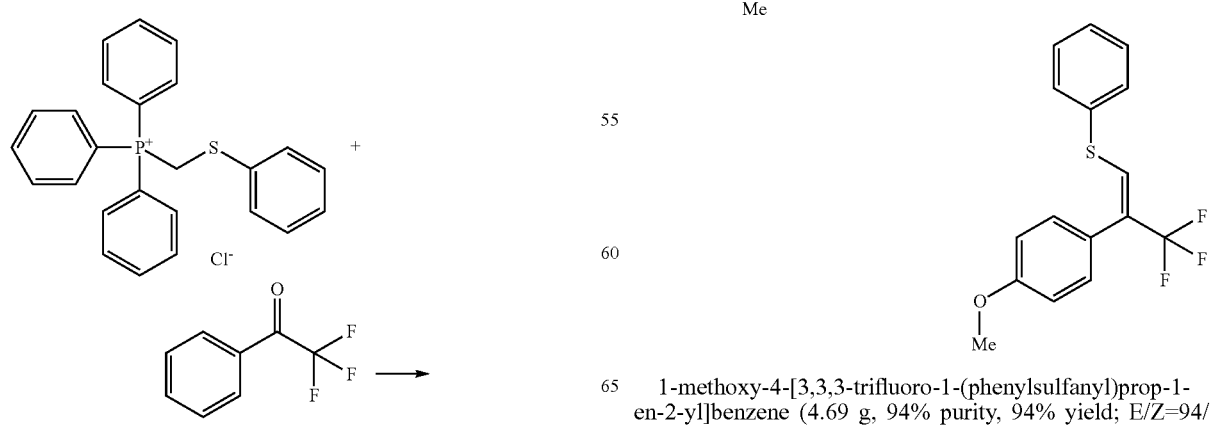

1-methoxy-4-[3,3,3-trifluoro-1-(phenylsulfanyl)prop-1-en-2-yl]benzene (4.69 g, 94% purity, 94% yield; E/Z=94/6—determined by GC, not assigned) was synthesized according to preparation example 1, using 2,2,2-trifluoro-1-(4-methoxyphenyl)ethanone (14.7 mmol).
MS (EI+): m/z=310.1 [M⁺].

PREPARATION EXAMPLE 1C

Step (i)—Preparation of 1 2-(4-chlorophenyl)-3,3,3-trifluoroprop-1-en-1-yl phenyl sulfide

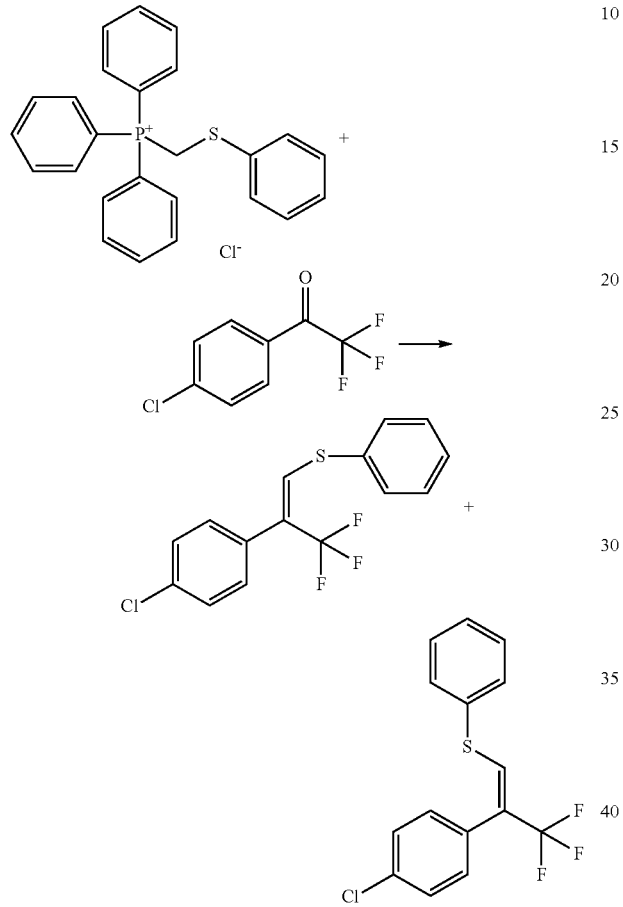

2-(4-Chlorophenyl)-3,3,3-trifluoroprop-1-en-1-yl phenyl sulfide (4.39 g, 91% purity, 89% yield; E/Z=91/9—determined by GC, not assigned) was synthesized according to preparation example 1, using 1-(4-chlorophenyl)-2,2,2-trifluoroethanone (14.4 mmol).
MS (EI+): m/z=314.1 [M⁺].

PREPARATION EXAMPLE 1D

Step (i)—Preparation of 1,2,3-trichloro-5-[3,3,3-trifluoro-1-(phenylsulfanyl)prop-1-en-2-yl]benzene

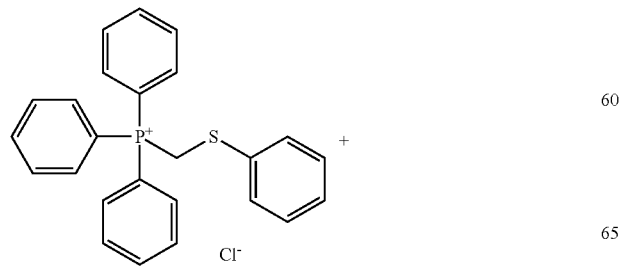

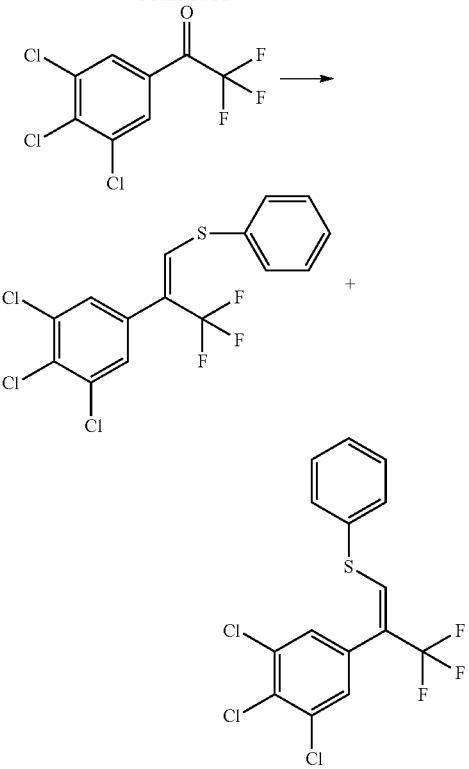

1,2,3-Trichloro-5-[3,3,3-trifluoro-1-(phenylsulfanyl)prop-1-en-2-yl] (6.71 g, 92% purity, 94% yield; E/Z=94/6—determined by GC, not assigned) was synthesized according to preparation example 1, using 2,2,2-trifluoro-1-(3,4,5-trichlorophenyl)ethanone (17.1 mmol).
MS (EI+): m/z=381.9 [M⁺].

PREPARATION EXAMPLE 2

Step (i-a)—Preparation of 2-(3,5-dichlorophenyl)-3,3,3-trifluoroprop-1-en-1-yl phenyl sulfoxide

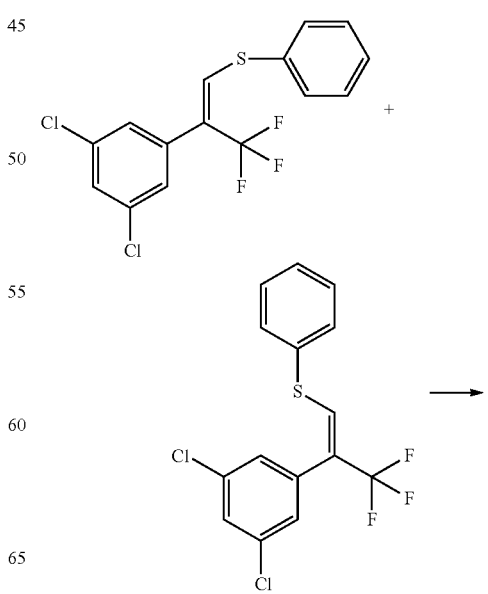

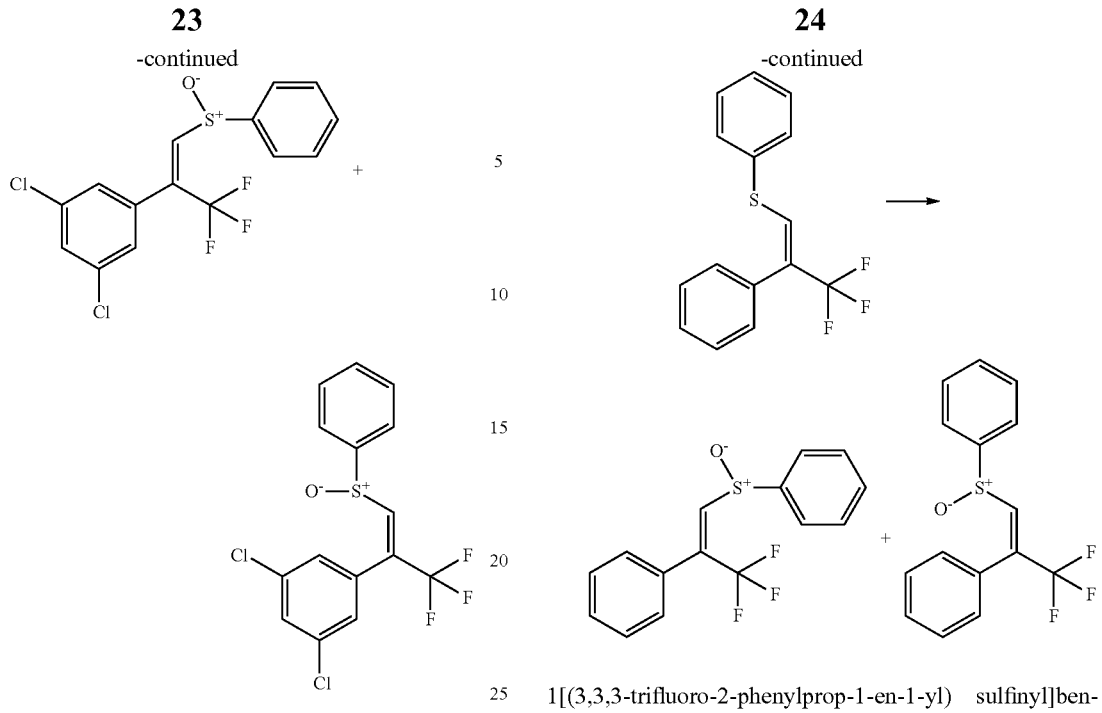

2-(3,5-Dichlorophenyl)-3,3,3-trifluoroprop-1-en-1-yl phenyl sulfide (1.00 g, 94% purity, 2.69 mmol) was dissolved in glacial acetic acid (5 mL) and hydrogen peroxide (0.54 mL, 35% in water, 6:19 mml) was added in one portion. The reaction mixture was heated to 50° C. and stirred for three hours at that temperature. After cooling, toluene and water were added and the phases were separated. The aqueous phase was extracted with toluene and the combined organic phases were washed two times with saturated sodium bicarbonate solution and once with sodium metabisulfite solution (30% w/w solution in water). Drying over sodium sulfate, filtration and evaporation yielded 2-(3,5-dichlorophenyl)-3,3,3-trifluoroprop-1-en-1-yl phenyl sulfoxide (950 mg, 94% purity, 91% yield, E/Z=93/7).

$^1$H-NMR (CDCl$_3$, 400 MHz): δ=7.12 (m, 1 H), 7.26 (s, 2H), 7.54 (m, 1H), 7.58 ppm (s, 5H); MS (EI+): m/z=364.0 [M$^+$].

The minor double bond isomer (Z) can be separated by crystallisation from propane-2-ol.

PREPARATION EXAMPLE 2A

Step (i-a)—Preparation of [(3,3,3-trifluoro-2-phenylprop-1-en-1-yl)sulfinyl]benzene 1[(3,3,3-trifluoro-2-phenylprop-1-en-1-yl) sulfinyl]benzene (481 mg, 98% purity, 95% yield; E/Z=94/6—not assigned) was synthesized according to preparation example 2, using [(3,3,3-trifluoro-2-phenylprop-1-en-1-yl)sulfanyl]benzene (1.68 mmol).

MS (EI+): m/z=296.0 [M$^+$].

PREPARATION EXAMPLE 2B

Step (i-a)—Preparation of 1-methoxy-4-[3,3,3-trifluoro-1-(phenylsulfinyl)prop-1-en-2-yl]benzene

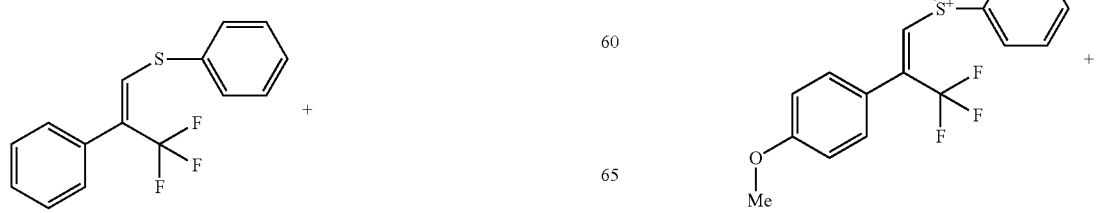

-continued

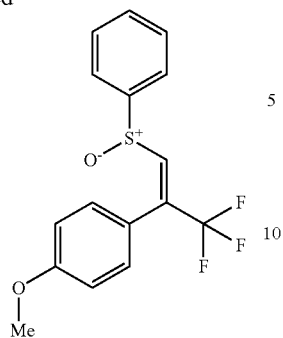

1-methoxy-4-[3,3,3-trifluoro-1-(phenylsulfinyl)prop-1-en-2-yl]benzene (478 mg, 95% purity, 92% yield; E/Z=96/4—not assigned) was synthesized according to preparation example 2, using 1-methoxy-4-[3,3,3-trifluoro-1-(phenylsulfanyl)prop-1-en-2-yl]benzene (1.51 mmol).

MS (EI+): m/z=326.1 [M$^+$].

PREPARATION EXAMPLE 2C

Step (i-a)—Preparation of 2-(4-chlorophenyl)-3,3,3-trifluoroprop-1-en-1-yl phenyl sulfoxide 2-(4-chlorophenyl)-3,3,3-trifluoroprop-1-en-1-yl phenyl sulfoxide (509 mg, 90% purity, 93% yield; E/Z=95/5—not assigned) was synthesized according to preparation example 2, using 2-(4-chlorophenyl)-3,3,3-trifluoroprop-1-en-1-yl phenyl sulfide (1.49 mmol).

MS (EI+): m/z=330.0 [M$^+$].

PREPARATION EXAMPLE 2D

Step (i-a)—Preparation of 1,2,3-trichloro-5-[3,3,3-trifluoro-1-(phenylsulfinyl)prop-1-en-2-yl]benzene

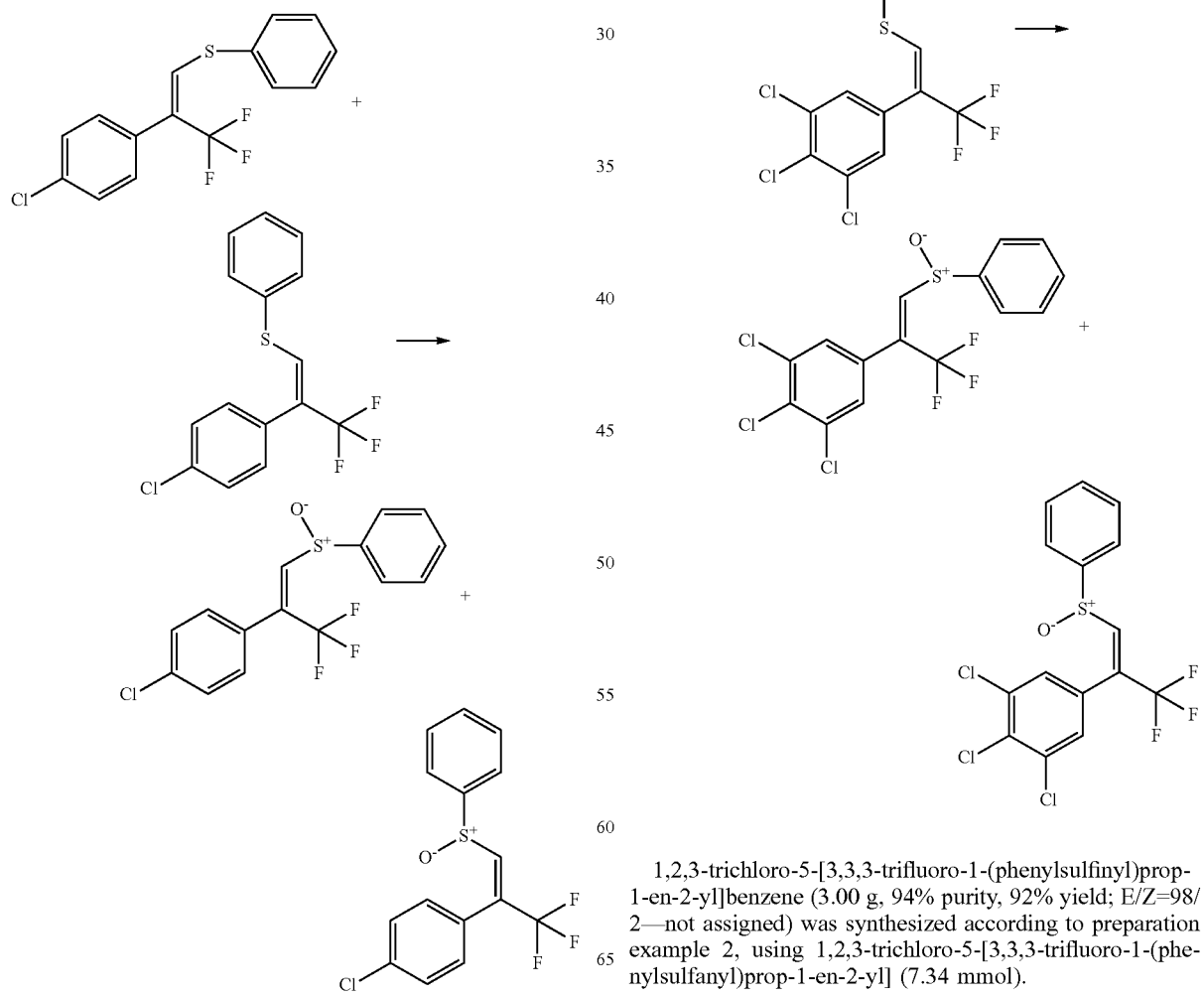

1,2,3-trichloro-5-[3,3,3-trifluoro-1-(phenylsulfinyl)prop-1-en-2-yl]benzene (3.00 g, 94% purity, 92% yield; E/Z=98/2—not assigned) was synthesized according to preparation example 2, using 1,2,3-trichloro-5-[3,3,3-trifluoro-1-(phenylsulfanyl)prop-1-en-2-yl] (7.34 mmol).

MS (EI+): m/z=397.9 [M$^+$].

PREPARATION EXAMPLE 3

Step (i)—Preparation of 2-(3,5-dichlorophenyl)-3,3,3-trifluoroprop-1-en-1-yl phenyl sulfoxide

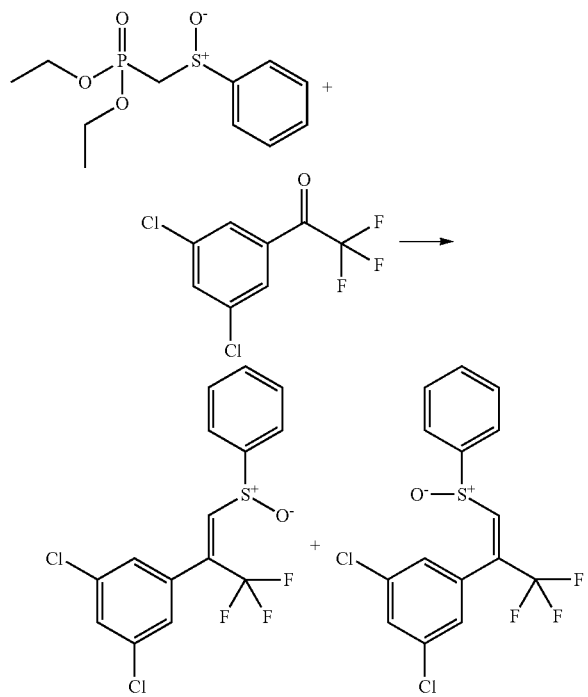

Diethyl [(phenylsulfinyl)methyl]phosphonate (5.00 g, 96% purity, 17.4 mmol) was dissolved in toluene (20 mL) and cooled to 0° C. To the solution potassium tert-butoxide (2.05 g, 18.2 mmol) was added in one portion. This solution was added over 45 minutes to a solution of 1-(3,5-Dichlorophenyl)-2,2,2-trifluoroethanone (4.26 g, 99% purity, 17.4 mmol) in toluene at 0° C. The reaction mixture was stirred for additional 15 minutes at 0° C. and then warmed to room temperature over 30 minutes. The solution was poured onto hydrochloric acid (3.6%) and the phases were separated. The aqueous phase was extracted with toluene and the combined organic phases were washed with water, dried over sodium sulfate and the solvents evaporated. 2-(3,5-dichlorophenyl)-3,3,3-trifluoroprop-1-en-1-yl phenyl sulfoxide was obtained (6.26 g, 94% purity, 93% yield, E/Z=38/62).

$^1$H-NMR (CDCl$_3$, 400 MHz): δ=6.68 (m, 1 H), 7.26 (s, 2H), 7.44 (m, 1H), 7.58 ppm (s, 5H); for NMR shifts of the E-stereoisomer and MS see preparation example 2.

PREPARATION EXAMPLE 4

Step (i)—Preparation of 2-(3,5-dichlorophenyl)-3,3,3-trifluoroprop-1-en-1-yl phenyl sulfoxide

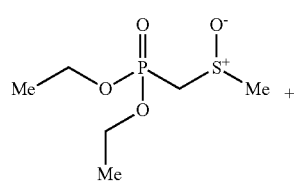

-continued

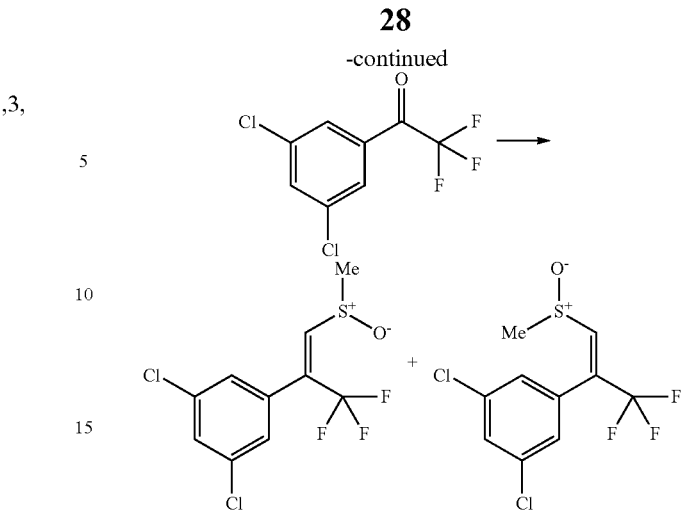

Magnesium chloride (dry, 2.19 g, 23.0 mmol) was put in a flask under argon atmosphere and dry acetonitrile (38 mL) was added. The mixture was stirred for five minutes at room temperature. Diethyl [(methylsulfinyl)methyl]phosphonate (4.75 g, 89% purity, 19.7 mmol) was added. After 10 minutes stirring the magnesium chloride was nearly dissolved. Triethylamine (3.44 mL, 24.7 mmol) was added and after 10 minutes at room temperature a slightly yellow solution was obtained. Then 1-(3,5-dichlorophenyl)-2,2,2-trifluoroethanone (4.10 g, 98% purity, 16.4 mmol) was added over 15 minutes showing pronounced exothermic behavior. After four hours methyl tert-buthyl ether (MTBE, 40 mL) and water (25 mL) were added and the phases were separated. After extracting the aqueous phase with MTBE (15 mL) the combined organic phases were washed with water, dried over sodium sulfate, filtered and the solvents evaporated. 2-(3,5-dichlorophenyl)-3,3,3-trifluoroprop-1-en-1-yl phenyl sulfoxide was obtained (5.22 g, 93% purity, 82% yield, Z/E=75/25). To further increase purity above 99% the crude material can be crystallised from n-heptane.

$^1$H-NMR (CDCl$_3$, 400 MHz): δ=2.73 (s, 3H, E-Isomer), 2.82 (s, 3H, Z-Isomer), 6.83 (s, 1H, Z-Isomer), 7.20 (m, 3H, E-Isomer), 7.30 (m, 2H, Z-Isomer), 7.47 (m, 1H, Z-Isomer), 7.50 ppm (m, 1H, E-Isomer); MS (EI+): m/z=302.0 [(M+1)$^+$].

PREPARATION EXAMPLE 5

Step (i)—Preparation of 2-(3,5-dichlorophenyl)-3,3,3-trifluoroprop-1-en-1-yl methyl sulfone

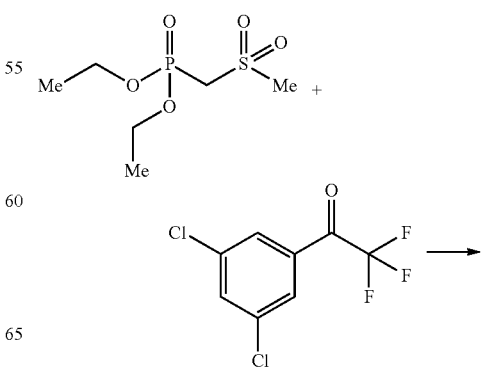

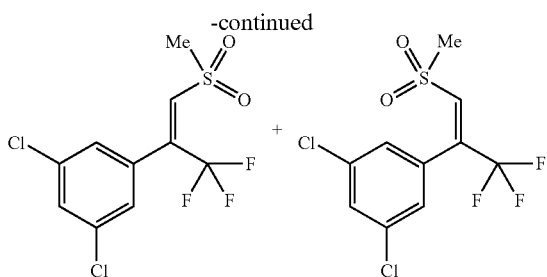

Magnesium chloride (dry, 241 mg, 2.53 mmol) was put in a flask under a nitrogen atmosphere and acetonitrile (3.5 mL) was added. The mixture was stirred for five minutes at room temperature. Diethyl [(methylsulfonyl)methyl]phosphonate (500 mg, 2.17 mmol) was added. After 10 minutes stirring the magnesium chloride was nearly dissolved. Triethylamine (378 µL, 2.72 mmol) was added and after 10 minutes at room temperature a slightly orange solution was obtained. Then 1-(3,5-dichlorophenyl)-2,2,2-trifluoroethanone (468 mg, 94% purity, 1.81 mmol) was added. After thirty minutes water (10 mL) and toluene (10 mL) were added and the phases were separated. After extracting the aqueous phase with toluene (10 mL) the combined organic phases were dried over sodium sulfate, filtered and the solvents evaporated. 2-(3,5-dichlorophenyl)-3,3,3-trifluoroprop-1-en-1-yl phenyl sulfone was obtained (540 g, >98% purity, 78% yield, E/Z (not assigned)=56/44).

$^1$H-NMR (CDCl$_3$, 400 MHz): δ=2.93 (s, 3 H, Isomer A), 3.20 (s, 3H, Isomer B), 6.82 (s, 1H, Isomer B), 7.16 (s, 1H, Isomer A), 7.28 (m, 2H, Isomer A), 7.29 (m, 2H, Isomer B), 7.50 (m, 1H, Isomer A), 7.52 ppm (m, 1H, Isomer B); MS (EI+): m/z=317.9 [(M+1)$^+$].

PREPARATION EXAMPLE 6

Step (i)—Preparation of 2-(3,5-dichlorophenyl)-3,3,3-trifluoroprop-1-en-1-yl phenyl sulfone

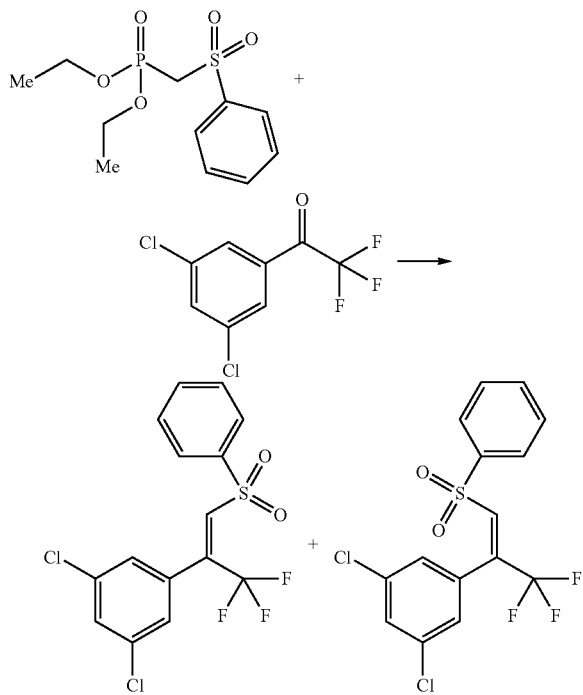

Magnesium chloride (dry, 3.16 g, 33.2 mmol) was put in a flask under a nitrogen atmosphere and acetonitrile (100 mL) was added. The mixture was stirred for five minutes at room temperature. Diethyl [(phenylsulfonyl)methyl]phosphonate (10.0 g, 89% purity, 30.4 mmol) was added. After 5 minutes stirring the magnesium chloride was nearly dissolved. Triethylamine (5.01 mL, 35.9 mmol) was added and after 10 minutes at room temperature a yellow solution was obtained. Then 1-(3,5-dichlorophenyl)-2,2,2-trifluoroethanone (6.89 mg, 98% purity, 27.7 mmol) was added. After stirring for one hour additional magnesium chloride (0.1 eq.) and triethylamine (0.1 eq.) were added and the mixture was stirred for additional 30 minutes. Then, additional triethylamine (0.1 eq.) was added. Water (100 mL) and ethyl acetate (200 mL) were added and the phases were separated. After extracting the aqueous phase twice with ethyl acetate (100 mL) the combined organic phases were washed three times with water (100 mL), three times with saturated sodium bicarbonate solution (100 mL), dried over sodium sulfate, filtered and the solvents evaporated. The yellow oil was recrystallized from n-heptane. 2-(3,5-dichlorophenyl)-3,3,3-trifluoroprop-1-en-1-yl phenyl sulfone was obtained (10.5 g, 97% purity, 98% yield, E/Z (not assigned)=64/36).

$^1$H-NMR (CDCl$_3$, 400 MHz): δ=6.80 (m, 1H, isomer B), 7.00 (m, 2H, isomer A), 7.22 (m, 2H, isomer B), 7.24 (m, 1H, isomer A), 7.42 (t, 1H, isomer A), 7.45 (t, 1H, isomer B), 7.50 (m, 1H, isomer A), 7.52 (m, 1H, isomer B), 7.61-7.67 (m, 6H, isomer A & B), 8.00 (m, 1H, isomer A), 8.02 ppm (m, 1H, isomer B); GC-MS (EI+): m/z=379.9 [M$^+$].

PREPARATION EXAMPLE 7

Step (i)—Preparation of 2-(3,5-dichlorophenyl)-3,3,3-trifluoroprop-1-en-1-yl methyl sulfide

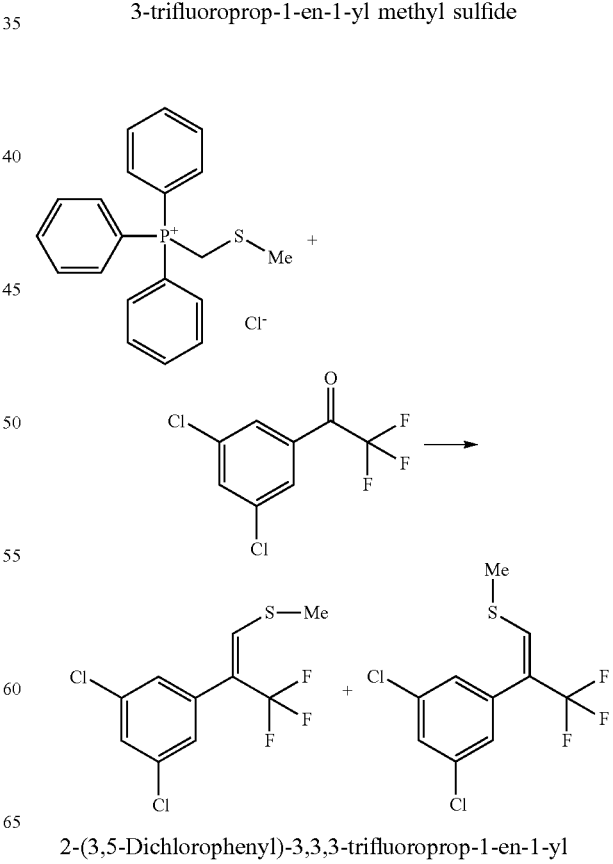

2-(3,5-Dichlorophenyl)-3,3,3-trifluoroprop-1-en-1-yl methyl sulfide (10.9 g, 97% purity, 90% yield; E/Z=86/14)

was synthesized according to preparation example 1, using 1-(3,5-dichlorophenyl)-2,2,2-trifluoroethanone (40.9 mmol).

$^1$H-NMR (DMSO-D$_6$, 599 MHz): δ=2.41 (s, 3H, E isom.), 2.47 (s, 3H, Z isom.), 6.78 (s, 1H, Z isom.), 7.14 (m, E isom.), 7.20 (m, 2H, Z isom.), 7.26 (m, 2H, E isom.), 7.32 (t, 1H, Z isom.), 7.37 ppm (t, 1H, E isom.); MS (EI+): m/z=286.0 [M$^+$].

PREPARATION EXAMPLE 8

Step (i-a)—Preparation of 2-(3,5-dichlorophenyl)-3,3,3-trifluoroprop-1-en-1-yl methyl sulfoxide

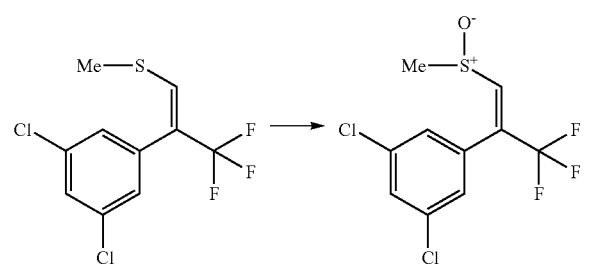 [SMILES: CS/C=C(\c1cc(Cl)cc(Cl)c1)C(F)(F)F ; C[S+]([O-])/C=C(\c1cc(Cl)cc(Cl)c1)C(F)(F)F]

2-(3,5-dichlorophenyl)-3,3,3-trifluoroprop-1-en-1-yl methyl sulfoxide (933 mg, >99% purity, 92% yield; E/Z=92/8) was synthesized according to preparation example 2, using (3,5-Dichlorophenyl)-3,3,3-trifluoroprop-1-en-1-yl methyl sulfide (3.36 mmol).

$^1$H-NMR (CDCl3, 400 MHz): δ=2.73 (s, 3H), 7.20 (m, 3H), 7.50 ppm (t, 1H); MS (EI+): m/z=302.9 [(M+1)$^+$].

PREPARATION EXAMPLE 9

Step (i-a)—Preparation of 2-(3,5-dichlorophenyl)-3,3,3-trifluoroprop-1-en-1-yl phenyl sulfone

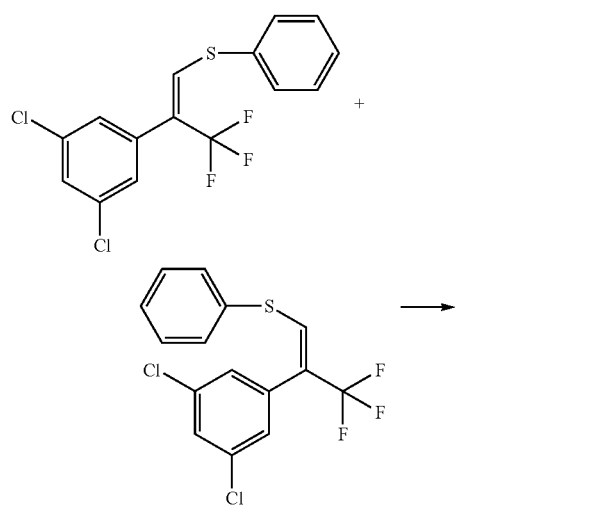

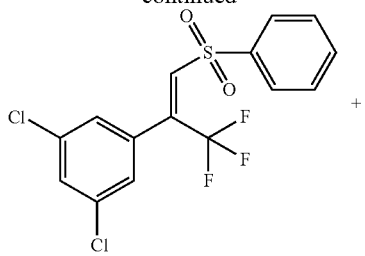

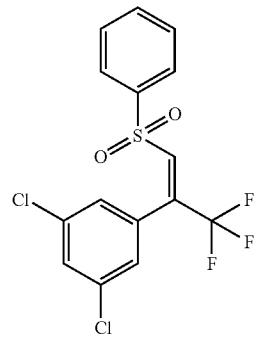

2-(3,5-Dichlorophenyl)-3,3,3-trifluoroprop-1-en-1-yl phenyl sulfide (2.00 g, 94% purity, 5.38 mmol) was dissolved in acetic acid (10 mL) and hydrogen peroxide (2.17 mL, 35% in water, 24.7 mmol) was added in one portion. The reaction mixture was stirred for eight hours, and then left standing for two days at room temperature. Then the reaction was heated to 50° C., but no further conversion took place. Upon cooling a white solid precipitated. The suspension was diluted with water (10 mL) and the solid was filtered off, washed twice with water and dried over night at 40° C. under vacuum. 2-(3,5-dichlorophenyl)-3,3,3-trifluoroprop-1-en-1-yl phenyl sulfone was obtained (1.82 g, 81% purity, 72% yield). A small portion of the product was crystallized from n-heptane to yield an analytical pure sample (96% purity).

$^1$H NMR (DMSO-D$_6$, 400 MHz): δ=7.32 (d, 2H), 7.61-7.67 (m, 2H), 7.72-7.79 (m, 4H), 8.01 ppm (m, 1H).

PREPARATION EXAMPLE 10

Step (ii-a)—Preparation of 1-benzyl-3-(3,5-dichlorophenyl)-4-(phenylsulfinyl)-3-(trifluoromethyl)-pyrrolidine

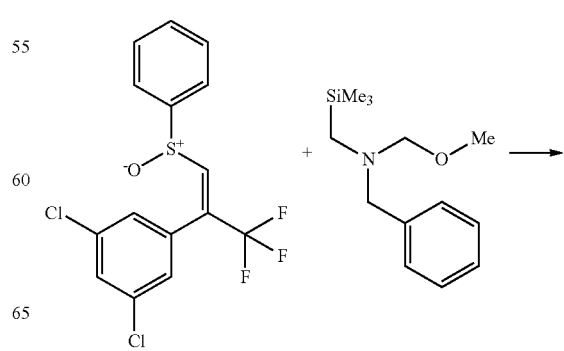

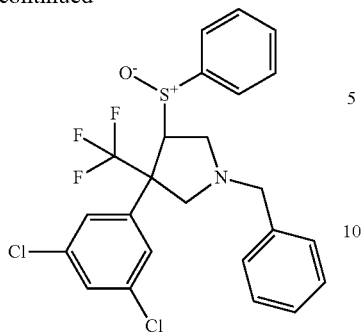

Trifluoroacetic acid (9 μL, 128 μmol) was added to (1E)-2-(3,5-dichlorophenyl)-3,3,3-trifluoroprop-1-en-1-yl phenyl sulfoxide (1.00 g, 93% purity, 2.56 mmol) in toluene (1.28 mL). N-Benzyl-1-methoxy-N-[(trimethylsilyl)methyl]methanamine (911 mg, 3.84 mmol) in toluene (8.75 mL) was added at room temperature over one hour. The solvents of the reaction mixture were removed and the crude product was taken up in iso-propanol and the pH was adjusted to 3 with 3.6% hydrochloric acid. After two hours the formed crystals were filtered off. 1-Benzyl-3-(3,5-dichlorophenyl)-4-(phenylsulfinyl)-3-(trifluoro-methyl)pyrrolidinium chloride (1.17 g, 95% purity, 86% yield) was obtained. The hydrochloride was suspended in aqueous sodium hydroxide (2 N, 5 mL) and ethyl acetate was added. The mixture was stirred until two clear phases were formed. The organic phase was separated, dried over sodium sulfate, filtered and evaporated. This procedure yielded 1-benzyl-3-(3,5-dichlorophenyl)-4-(phenylsulfinyl)-3-(trifluoromethyl)pyrrolidine (1.07 g, 95% purity, 80% yield).

$^1$H-NMR (CDCl$_3$, 600 MHz): δ=2.82 (dd, 1H), 3.12 (s, 2H), 3.66 (m, 2H), 3.72 (dd, 1H), 3.86 (d, 1H), 7.24-7.53 ppm (m, 13H); MS (EI+): m/z=497.1 [(M+1)$^+$].

PREPARATION EXAMPLE 10A

Step (ii-a)—Preparation of 1-benzyl-3-phenyl-4-(phenylsulfinyl)-3-(trifluoromethyl)pyrrolidine

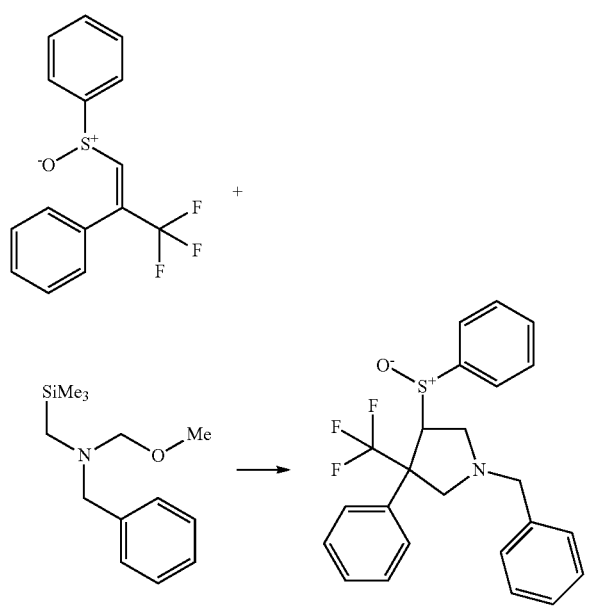

1-benzyl-3-phenyl-4-(phenylsulfinyl)-3-(trifluoromethyl)pyrrolidine (433 mg, 97% purity, 63% yield) was synthesized according to preparation example 10, using [(3,3,3-trifluoro-2-phenylprop-1-en-1-yl)sulfinyl]benzene (1.54 mmol).

$^1$H NMR (CDCl$_3$, 400 MHz): δ=2.91 (dd, 1H), 3.25 (d, 1H), 3.33 (d, 1H), 3.46 (dd, 1H), 3.72 (m, 2H), 3.86 (d, 1H), 7.28-7.63 ppm (m, 15H); MS (EI+): m/z=430.0 [(M+1)$^+$].

PREPARATION EXAMPLE 10B

Step (ii-a)—Preparation of 1-benzyl-3-(4-methoxyphenyl)-4-(phenylsulfinyl)-3-(trifluoromethyl)pyrrolidine

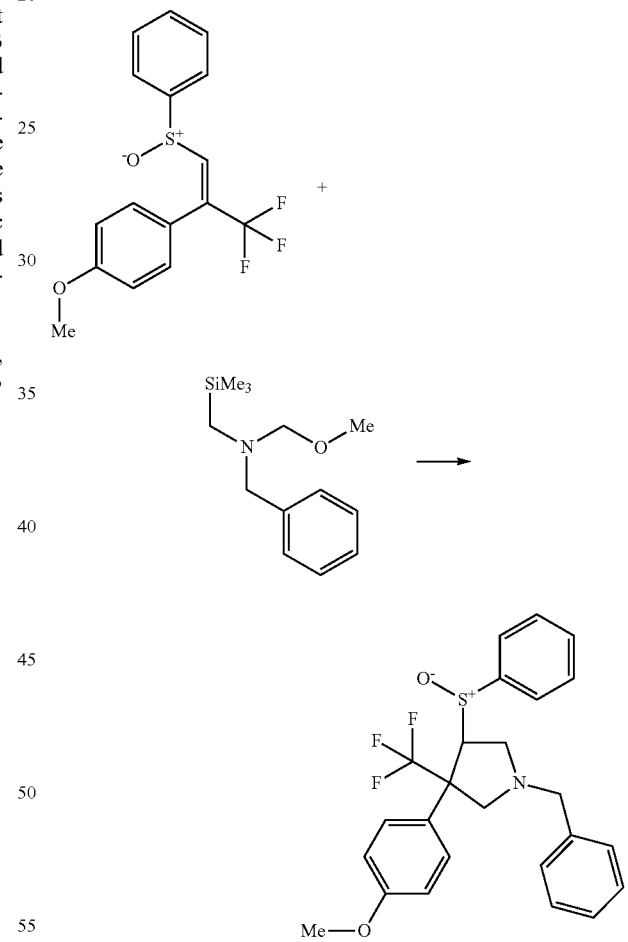

1-benzyl-3-(4-methoxyphenyl)-4-(phenylsulfinyl)-3-(trifluoromethyl)pyrrolidine (161 mg, >98% purity, 28% yield) was synthesized according to preparation example 10, using 1-methoxy-4-[3,3,3-trifluoro-1-(phenylsulfinyl)prop-1-en-2-yl]benzene (1.23 mmol).

$^1$H-NMR (CDCl$_3$, 400 MHz): δ=2.88 (dd, 1H), 3.20 (d, 1H), 3.31 (d, 1H), 3.41 (dd, 1H), 3.68 (dd, 1H), 3.73 (d, 1H), 3.83 (s, 3H), 3.84 (d, 1H), 6.91 (d, 2H), 7.27-7.50 ppm (m, 12H); MS (EI+): m/z=460.1 [(M+1)$^+$].

PREPARATION EXAMPLE 10C

Step (ii-a)—Preparation of 1-benzyl-3-(4-chlorophenyl)-4-(phenylsulfinyl)-3-(trifluoromethyl)pyrrolidine

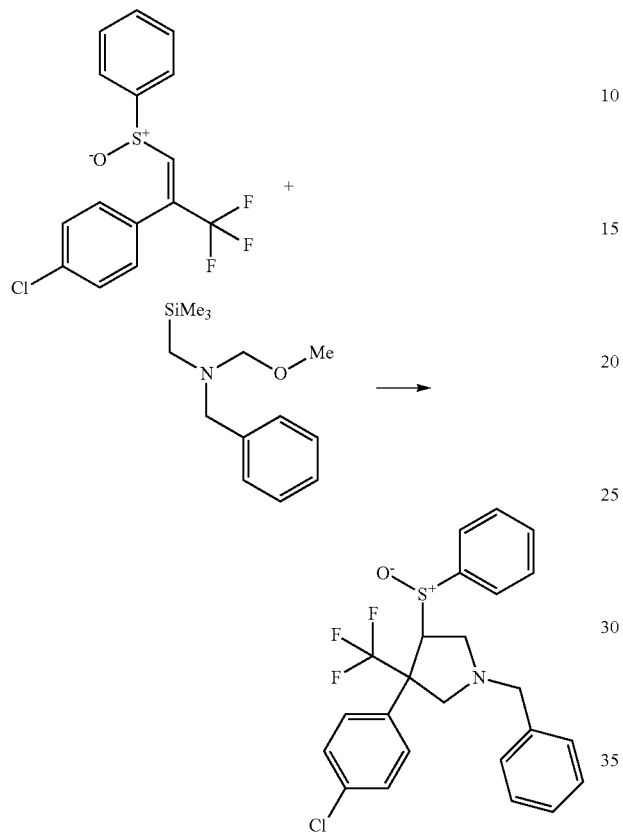

1-benzyl-3-(4-chlorophenyl)-4-(phenylsulfinyl)-3-(trifluoromethyl)pyrrolidine (502 mg, 94% purity, 80% yield) was synthesized according to preparation example 10, using 1,2,3-trichloro-5-[3,3,3-trifluoro-1-(phenylsulfinyl)prop-1-en-2-yl]benzene (1.27 mmol).

$^1$H-NMR (CDCl$_3$, 400 MHz): δ=2.85 (dd, 1H), 3.19 (d, 1H), 3.27 (d, 1H), 3.47 (dd, 1H), 3.68 (dd, 1H), 3.71 (d, 1H), 3.85 (d, 1H), 7.21-7.55 ppm (m, 14H); MS (EI+): m/z=464.0 [(M+1)$^+$].

PREPARATION EXAMPLE 10D

Step (ii-a)—Preparation of 1-benzyl-4-(phenylsulfinyl)-3-(3,4,5-trichlorophenyl)-3-(trifluoromethyl)-pyrrolidine

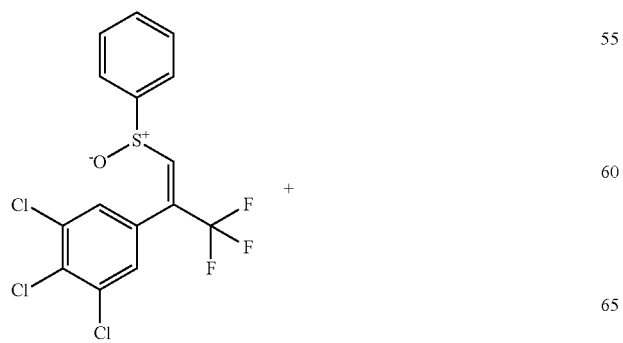

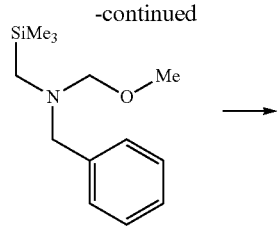

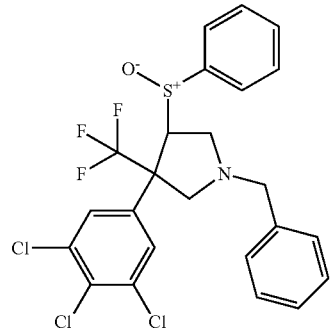

1-benzyl-4-(phenylsulfinyl)-3-(3,4,5-trichlorophenyl)-3-(trifluoromethyl)pyrrolidine (203 mg, 92% purity, 58% yield) was synthesized according to preparation example 10, using 1,2,3-trichloro-5-[3,3,3-trifluoro-1-(phenylsulfinyl)prop-1-en-2-yl]benzene (683 μmol).

$^1$H-NMR (CDCl$_3$, 400 MHz): δ=2.77 (dd, 1H), 3.10 (m, 2H), 3.56-3.67 (m, 3H), 3.94 (d, 1H), 7.24-7.49 (m, 10H), 7.70 ppm (s, 2H); MS (EI+): m/z=531.0 [M$^+$].

PREPARATION EXAMPLE 11

Step (ii-a)—Preparation of 1-benzyl-3-(3,5-dichlorophenyl)-4-(methylsulfinyl)-3-(trifluoromethyl)-pyrrolidine

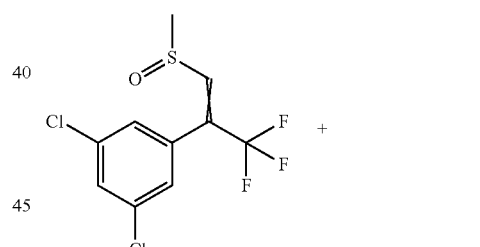

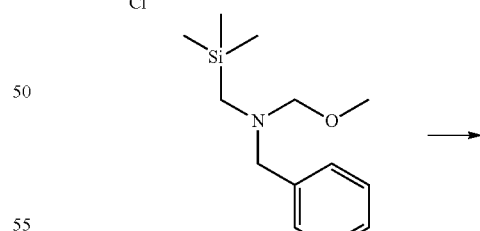

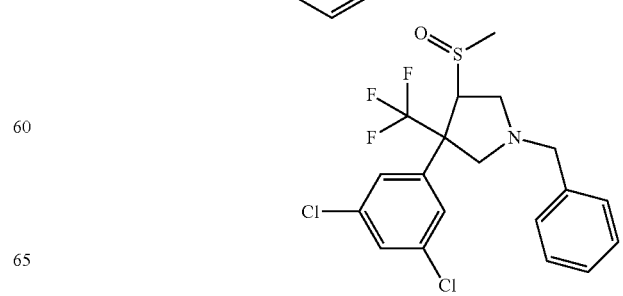

Trifluoroacetic acid (61 μL, 816 μmol) was added to 2-(3,5-dichlorophenyl)-3,3,3-trifluoroprop-1-en-1-yl phenyl (5.22 g, 95% purity, 16.3 mmol) in toluene (17 mL). N-Benzyl-1-methoxy-N-[(trimethylsilyl)methyl]methanamine (5.81 g, 24.5 mmol) in toluene (70 mL) was added at room temperature over one hour. After stirring for three hours at room temperature toluene was distilled off under reduced pressure to yield crude product which slowly crystallized upon standing. Parts of the crude product (5 g) were dissolved in 2-propanol and 2 N hydrochloric acid was used to adjust the pH to 3. The solid precipitate was filtered off to yield 1-benzyl-3-(3,5-dichlorophenyl)-4-(methylsulfinyl)-3-(trifluoromethyl)pyrrolidine hydrochloride (2.45 g, 86% purity, 52% yield).

$^1$H-NMR (CDCl$_3$, 400 MHz): δ=2.53 (s, 3H), 3.12 (d, 1H), 3.30 (m, 3H), 3.44 (t, 1H), 3.70 (d, 1H), 3.85 (t, 1H), 7.28-7.39 (m, 6H), 7.40 ppm (m, 2H); MS (EI+): m/z=435.1 [M$^+$].

PREPARATION EXAMPLE 12

Step (ii-a)—Preparation of 1-benzyl-3-(3,5-dichlorophenyl)-4-(phenylsulfonyl)-3-(trifluoromethyl)-pyrrolidine

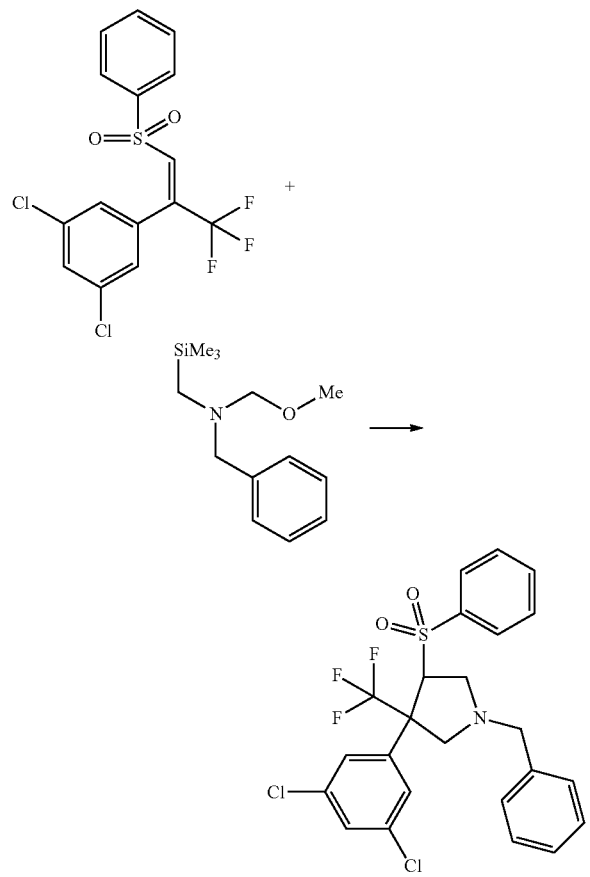

Trifluoroacetic acid (38 μL, 513 μmol) was added to (1E)-2-(3,5-dichlorophenyl)-3,3,3-trifluoroprop-1-en-1-yl phenyl sulfoxide (4.00 g, 98% purity, 10.3 mmol) in toluene (20 mL). N-Benzyl-1-methoxy-N-[(trimethylsilyl)methyl] methanamine (3.65 g, 15.4 mmol) in toluene (18 mL) was added at room temperature over two hours. After two more hours additional N-Benzyl-1-methoxy-N-[(trimethylsilyl)-methyl]methanamine (0.2 eq.) was added and the reaction left stirring for another hour. The solvents of the reaction mixture were removed and the crude product was taken up in n-heptane. The formed crystals were filtered off. 1-Benzyl-3-(3,5-dichlorophenyl)-4-(phenylsulfinyl)-3-(trifluoromethyl)-pyrrolidinium chloride (4.40 g, >99% purity, 83% yield, E/Z [not assigned]=53/47) was obtained.

$^1$H NMR (CDCl$_3$, 400 MHz): δ=2.92 (d, 1H), 2.95 (t, 1H), 2.97 (d, 1H), 3.10 (t, 1H), 3.19 (d, 2H), 3.41 (d, 1H), 3.55 (d, 1H), 3.64 (d, 1H), 3.76 (m, 1H), 3.78 (d, 1H), 3.86 (d, 1H), 4.04 (dd, 1H), 4.20 (dd, 1H), 7.26-7.76 (m, 24H), 6.90 (m, 1H), 7.92 ppm (m, 1H) [Peaks for both isomers]; MS (EI−): m/z=512.0 [(M−1)$^+$].

PREPARATION EXAMPLE 13

Step (ii-a)—Preparation of 1-benzyl-3-(3,5-dichlorophenyl)-4-(methylsulfonyl)-3-(trifluoromethyl)-pyrrolidine

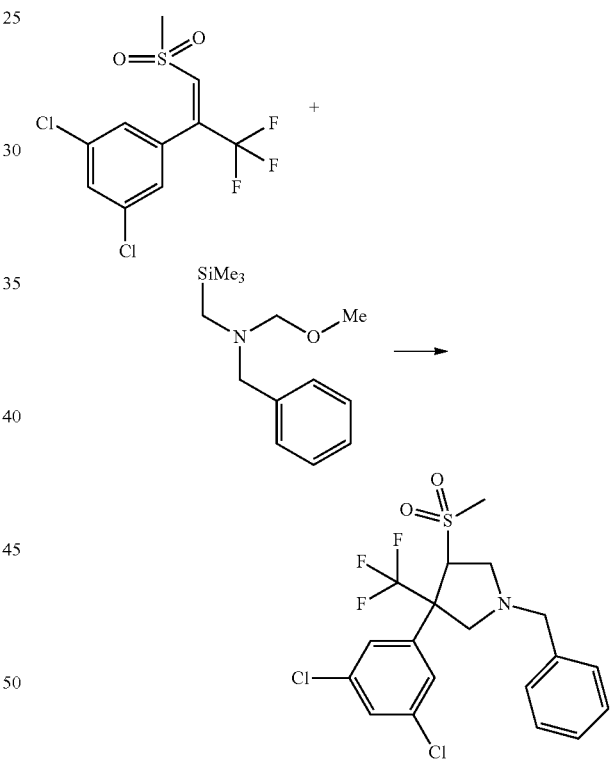

Trifluoroacetic acid (6 μL, 78 μmol) was added to 2-(3,5-Dichlorophenyl)-3,3,3-trifluoroprop-1-en-1-yl methyl sulfone (500 mg, 1.57 mmol) in toluene (3 mL). N-Benzyl-1-methoxy-N-[(trimethylsilyl)methyl]methanamine (558 mg, 2.35 mmol) in toluene (2 mL) was added at room temperature over 10 minutes. The reaction mixture was stirred for two hours and then additional N-Benzyl-1-methoxy-N-[(trimethylsilyl)methyl]methanamine (74.4 mg, 313 μmol) was added. The reaction mixture was stirred for additional two hours and then left standing over night. Water was added and after stirring for a while the phases were separated and the aqueous phase was extracted with toluene. The combined organic phases were dried over sodium sulfate and evaporated. The crude product is taken up in warm isopropanol (1 mL) and 10% hydrochloric acid (0.5 mL) and a drop of methanol was added. The formed crystals were filtered off. The hydrochloride was suspended in water and sodium hydroxide and tert-buthyl methylether was added. The organic phase was separated and the aqueous phase was extracted with tert-buthyl methylether. The combined organic phases were dried over sodium sulfate, filtered and evaporated. This procedure yielded 1-benzyl-3-(3,5-dichlorophenyl)-4-(methylsulfonyl)-3-(trifluoromethyl)pyrrolidine (302 mg, 99% purity, 42% yield).

$^1$H-NMR (CDCl$_3$, 400 MHz): δ=2.42 (s, 3H, isomer A), 2.97 (d, 1H, isomer A), 3.01 (s, 3H isomer B), 3.04 (dd, 1H, isomer A), 3.14-3.21 (m, 1H, isomer B), 3.30-3.37 (m, 4H, isomers A & B), 3.60 (dd, 1H, isomer A), 3.66 (d, 1H, isomer A), 3.69 (d, 1H, isomer B), 3.81 (d, 1H, isomer B), 3.87 (d, 1H, isomer A), 3.94-4.92 (m, 2H, isomer A & B), 7.29-7.42 (m, 12 H, isomer A & B), 7.54 (d, 2H, isomer B), 7.79 ppm (d, 2H, isomer A); MS (EI+): m/z=452.1 [(M+1)$^+$] for both peaks.

PREPARATION EXAMPLE 14

Step (iii-a-1) 1-benzyl-3-(3,5-dichlorophenyl)-3-(trifluoromethyl)-2,3-dihydro-1H-pyrrole

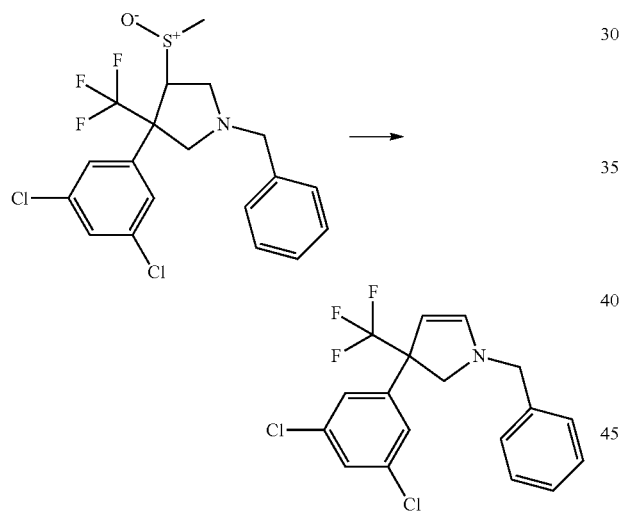

1-Benzyl-3-(3,5-dichlorophenyl)-4-(methylsulfonyl)-3-(trifluoromethyl)pyrrolidine (2.00 g, 95% purity, 4.13 mmol) was dissolved in toluene (40 mL) under a nitrogen atmosphere and sodium carbonate (1.31 g, 12.4 mmol) was added. The reaction mixture was heated to reflux for 150 minutes and cooled to room temperature. Water (20 mL) was added, the mixture stirred for 5 minutes and the phases separated. The water phase was extracted with toluene (20 mL) and solvent of the combined organic phases was evaporated under vacuum. The crude material was dissolved in warm n-heptane and after standing and cooling the forming crystals were filtered off to yield 1-benzyl-3-(3,5-dichlorophenyl)-3-(trifluoromethyl)-2,3-dihydro-1H-pyrrole (972 mg, 95% purity, 60% yield).

$^1$H-NMR (CDCl$_3$, 400 MHz): δ=3.36 (d, 1H), 3.72 (d, 1H), 3.99 (d, 1H), 4.16 (d, 1H), 5.18 (d, 1H), 6.63 (d, 1H), 7.28 (m, 3H), 7.34 (m, 2H), 7.46 (m, 2H), 7.60 ppm (m, 1H); GC-MS (EI+): m/z=371.0 [M$^+$].

PREPARATION EXAMPLE 15

(Step iii-a)—Preparation of a Compound of General Formula (I)

Step (iii-a-1) 1-benzyl-3-(3,5-dichlorophenyl)-3-(trifluoromethyl)-2,3-dihydro-1H-pyrrole

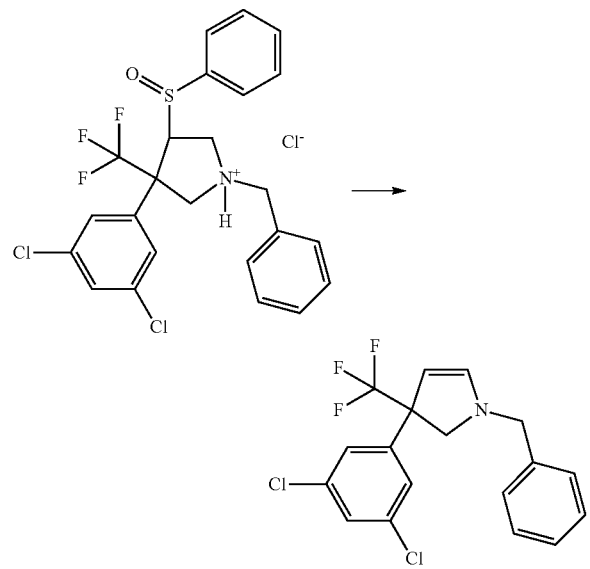

1-Benzyl-3-(3,5-dichlorophenyl)-4-(phenylsulfinyl)-3-(trifluoromethyl)pyrrolidinium chloride (1.00 g, 82% purity, 1.53 mmol) is suspended in toluene (3 mL) under a nitrogen atmosphere. Sodium carbonate (810 mg, 7.65 mmol) was added and the mixture was heated to reflux for 2.5 hours. After cooling water was added, the phases were separated and the aqueous phase was extracted twice with toluene. The combined organic phases were dried over sodium sulphate, filtered and the solvent evaporated. The residue was repeatedly crystallized from n-heptane to yield 1-benzyl-3-(3,5-dichlorophenyl)-3-(trifluoromethyl)-2,3-dihydro-1H-pyrrole (198 mg, 89% purity, 31% yield).

The analytical data is identical to those obtained in preparation example 14.

Step (iii-a-2) 1-benzyl-3-(3,5-dichlorophenyl)-3-(trifluoromethyl)pyrrolidine

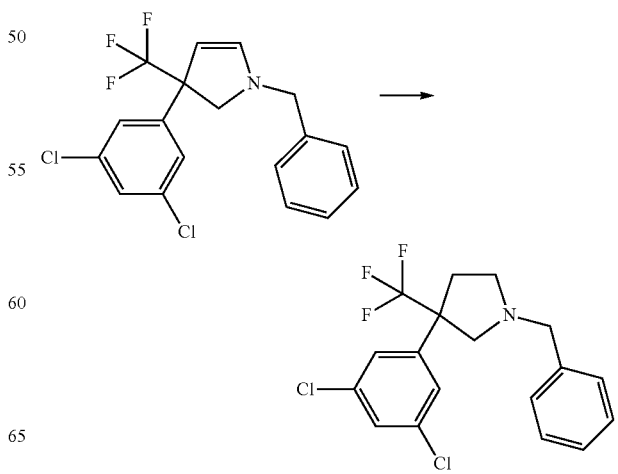

Alternative 1

1-Benzyl-3-(3,5-dichlorophenyl)-3-(trifluoromethyl)-2,3-dihydro-1H-pyrrole (200 mg, 82% purity, 440 µmol) was dissolved in methanol (5 mL) under an argon atmosphere. Formic acid (200 µL, 5.30 mmol) and platinum on charcoal (5 w/w % Pt/C, ~60% H$_2$O, 42.9 mg, 4.4 µmol) was added and the flask was charged with hydrogen (balloon). The reaction was stirred for six hours at room temperature and then left standing over night. After the addition of platinum on charcoal (0.5 mol %) and formic acid (1 mL) the reaction mixture was warmed to 40-50° C. for six hours and then left standing at room temperature. Refluxing the mixture for three more hours and addition of more platinum on charcoal (1.0 mol %) after one hour led to complete conversion. The reaction mixture was cooled to room temperature, diluted with ethyl acetate (5 mL), filtered over celite, washed with saturated sodium bicarbonate and brine solution. The organic phase was dried over sodium sulfate, filtered and the solvents evaporated. 1-benzyl-3-(3,5-dichlorophenyl)-3-(trifluoromethyl)pyrrolidine was obtained (163 mg, 97% purity, 96% yield).

The analytical data is identical to the spectroscopic data reported in WO 2008/129811 A1.

Alternative 2

1-Benzyl-3-(3,5-dichlorophenyl)-3-(trifluoromethyl)-2,3-dihydro-1H-pyrrole (100 mg, 90% purity, 242 µmol) was dissolved in tetrahydrofurane (2 mL) and sodium borohydride (26.0 mg, 677 µmol) was added at room temperature. After 30 minutes at room temperature the reaction mixture was acidified with hydrochloric acid (3.6%) and extracted twice with dichloromethane. The combined organic phases were washed with water, dried over sodium sulfate, filtered and the solvents evaporated. This procedure yielded 1-benzyl-3-(3,5-dichlorophenyl)-3-(trifluoromethyl)pyrrolidine (80.0 mg, 79% purity, 70% yield).

The analytical data is identical to the spectroscopic data reported in WO 2008/129811 A1.

PREPARATION EXAMPLE 16

(Step iii-a)—Preparation of a Compound of General Formula (I)

Step (iii-b) 1-benzyl-3-(3,5-dichlorophenyl)-3-(trifluoromethyl)pyrrolidine

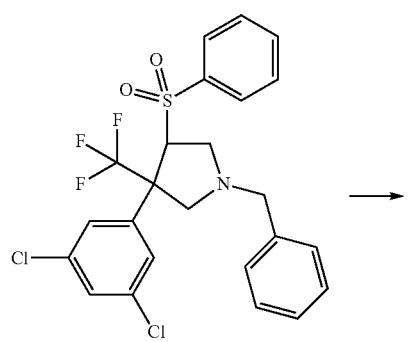

→

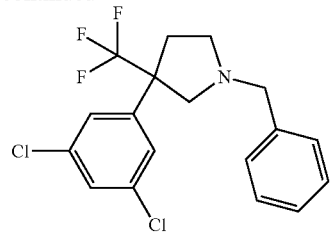

Magnesium (47.3 mg, 1.94 mmol), lithium chloride (41.2 mg, 972 µmol) and 1-benzyl-3-(3,5-dichlorophenyl)-4-(phenylsulfonyl)-3-(trifluoromethyl)pyrrolidine (500 mg, 972 µmol) were put in a flask under argon atmosphere. Methanol (5 mL) was added and the reaction was stirred for 4.5 hours and one additional hour after adding more magnesium (2 eq.). After standing over night the reaction was heated to 45° C. for seven hours adding magnesium (1 eq. each) after two and five hours. Again after standing over night magnesium was added (1 eq.) and the reaction heated to 45° C. for three hours. Water (2 mL) and methanol was added. After cooling to room temperature sodium hydroxide solution (10%) was added. The precipitate was filtered off, dissolved in ethyl acetate and methanol, washed with hydrochloric acid (10%). The organic phase was dried over sodium sulfate, filtered and the solvents evaporated. The crude 1-benzyl-3-(3,5-dichlorophenyl)-3-(trifluoromethyl)pyrrolidine (308 mg, 69% purity, 59% yield) was crystallized from iso-propanol (111 mg, 95% purity, 29% yield).

The analytical data is identical to the spectroscopic data reported in WO 2008/129811 A1.

The invention claimed is:

1. Process for the preparation of a compound of formula (X)

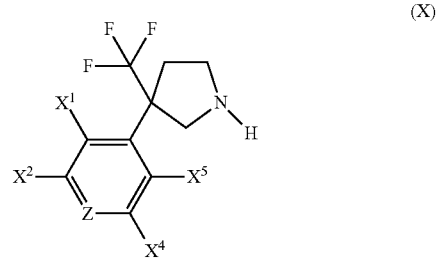

wherein

Z represents C—X$^3$ or a nitrogen atom,

X$^1$, X$^2$, X$^3$, X$^4$ and X$^5$ independently of each other are selected from the group consisting of hydrogen, halogen, cyano, C$_1$-C$_{12}$-alkyl, C$_1$-C$_{12}$-haloalkyl, C$_1$-C$_{12}$-alkoxy and C$_1$-C$_{12}$-haloalkoxy;

comprising step (i): reacting a compound of formula (II)

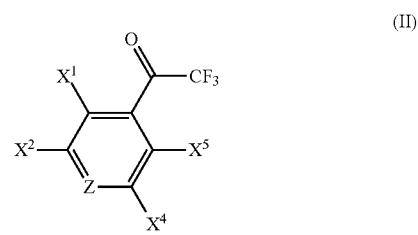

in which

X$^1$, X$^2$, X$^4$, X$^5$ and Z have the above mentioned meanings, with a compound of formula (III)

T-CH$_2$—S(O)$_m$R     (III)

in which

T is an anion stabilizing group;

R is $C_{1-12}$-alkyl, $C_{1-6}$-haloalkyl, phenyl, or phenyl-$C_{1-6}$-alkyl;

m is 0, 1 or 2;

optionally in the presence of a solvent, in the presence of a base and optionally in the presence of an additive, to obtain a compound of formula (IV),

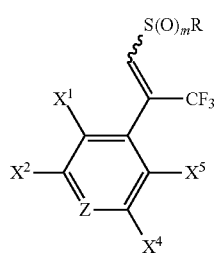

(IV)

in which $X^1$, $X^2$, $X^4$, $X^5$, R, m and Z have the above mentioned meanings, step (ii): reacting a compound of formula (IV), (ii-a) with a compound of formula (V)

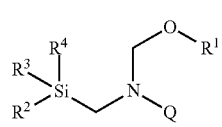

(V)

in which $R^1$ is selected from the group consisting of $C_{1-12}$-alkyl, $C_{1-6}$-haloalkyl, phenyl, and phenyl-$C_{1-6}$-alkyl;

$R^2$, $R^3$ and $R^4$ independently of each other are selected from the group consisting of $C_{1-12}$-alkyl, $C_{1-6}$-haloalkyl, phenyl, and phenyl-$C_{1-6}$-alkyl;

Q is selected from the group consisting of aryl-$C_1$-$C_6$-alkyl, $C_1$-$C_6$-alkoxy-($C_1$-$C_6$)-alkyl, $C_1$-$C_6$-alkyl-(O—$CH_2)_n$, and $C_2$-$C_6$-alkenyl;

in the presence of an acid or a fluoride salt; or (ii-b) with a compound of formula (Va)

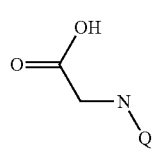

(Va)

in which

Q has the above mentioned meanings, in the presence of formaldehyde or a formaldehyde equivalent, and in the presence of a solvent, in which process the water formed during the reaction is removed from reaction mixture, to obtain a compound of formula (VI)

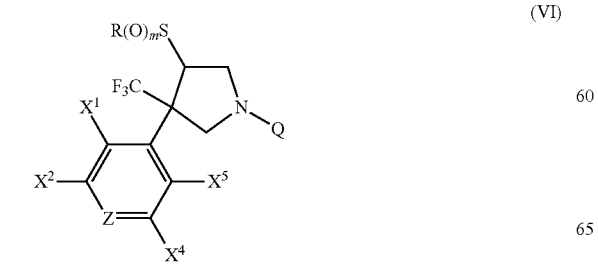

(VI)

in which $X^1$, $X^2$, $X^4$, $X^5$, R, m, Q and Z have the above mentioned meanings, which is converted into a compound of formula (I)

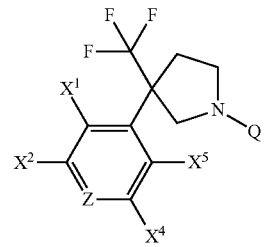

(I)

in which $X^1$, $X^2$, $X^4$, $X^5$, Q and Z have the above mentioned meanings, by (iii-a)

heating a compound of formula (VI) in which m represents 1, optionally in the presence of a base, if appropriate in the presence of a solvent (iii-a-1), to obtain a compound of formula (VII)

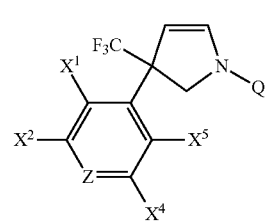

(VII)

in which $X^1$, $X^2$, $X^4$, $X^5$, Q and Z have the above mentioned meanings, which is subjected to a catalytic hydrogenation, or to a reduction reaction using a hydride source in an appropriate solvent (iii-a-2) or, by (iii-b)

removing the $S(O)_mR$ group by reacting a compound of formula (VI) in which m represents 2, with an elemental metal in the presence of a solvent, and optionally in the presence of a metal salt; or, by(iii-c)

removing the $S(O)_mR$ group from a compound of formula (VI) in which m represents 0 or 1 by catalytic hydrogenation in the presence of a solvent and optionally a base optionally comprising triethylamine or sodium carbonate or an acid optionally comprising hydrochloric acid, acetic acid, and (iv)

replacement of group Q by hydrogen to obtain a compound of formula (X), or reacting a compound of formula (IV) (ii-aa) with a compound of formula (V-1)

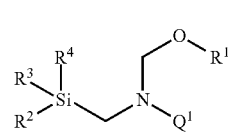

(V-1)

in which $R^1$, $R^2$, $R^3$ and $R^4$ have the above mentioned meanings and $Q^1$ is selected from the group consisting of $C_1$-$C_6$-alkyl-$(O-CH_2)_n$, or $R^1$ and $Q^1$ together with the atoms to which they are attached form a ring selected from

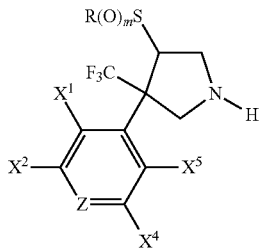

wherein the dotted line is the bond to the carbon atom adjacent to the Si-atom in formula (V-1);

in the presence of an acid or a fluoride salt
to obtain a compound of formula (VIa)

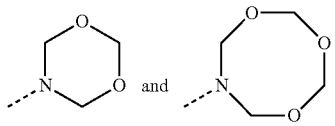

(VIa)

in which $X^1$, $X^2$, $X^4$, $X^5$, R, m and Z have the above mentioned meanings, which are converted into a compound of formula (X) by (iii-aa)

heating a compound of formula (VIa) in which m represents 1, optionally in the presence of a base, if appropriate in the presence of a solvent (iii-aa-1), to obtain a compound of formula (VIIa)

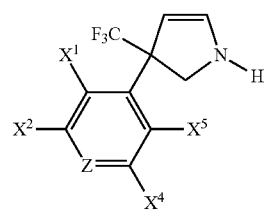

(VIIa)

in which $X^1$, $X^2$, $X^4$, $X^5$ and Z have the above mentioned meanings, which is subjected to a catalytic hydrogenation, or to a reduction reaction using a hydride source in an appropriate solvent (iii-aa-2).

2. The process according to claim 1, wherein Q is methylphenyl, $X^1$ is H, $X^2$ is Cl, $X^3$ is H, $X^4$ is Cl, $X^5$ is H, and Z is C—$X^3$.

3. The process according to claim 1, wherein Z is a nitrogen atom.

4. The process according to claim 1, wherein Z is C—$X^3$.

5. The process according to claim 1, comprising step (ii-a).

6. The process according to claim 1, comprising step (ii-b).

7. The process according to claim 1, comprising step (iii-a).

8. The process according to claim 1, comprising step (iii-b).

9. The process according to claim 1, comprising step (iii-c).

10. The process according to claim 1, comprising step (iii-aa).

11. The process according to claim 1, wherein $X^1$, $X^2$, $X^3$, $X^4$ and $X^5$ independently of each other are selected from the group consisting of hydrogen, fluorine, chlorine, trifluoromethyl or methoxy.

* * * * *